US011464712B2

(12) United States Patent
Hoch et al.

(10) Patent No.: US 11,464,712 B2
(45) Date of Patent: Oct. 11, 2022

(54) APPARATUS, DEVICE, AND METHOD FOR INFANT GAVAGE FEEDING

(71) Applicant: LOMA LINDA UNIVERSITY, Loma Linda, CA (US)

(72) Inventors: Erin Hoch, Loma Linda, CA (US); Eric C. Gosink, Loma Linda, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 232 days.

(21) Appl. No.: 16/430,634

(22) Filed: Jun. 4, 2019

(65) Prior Publication Data
US 2019/0282451 A1     Sep. 19, 2019

Related U.S. Application Data

(63) Continuation-in-part of application No. PCT/US2019/021334, filed on Mar. 8, 2019.
(Continued)

(51) Int. Cl.
*A61J 9/00* (2006.01)
*A61J 15/00* (2006.01)
(Continued)

(52) U.S. Cl.
CPC ......... *A61J 11/0005* (2013.01); *A61J 7/0053* (2013.01); *A61J 9/00* (2013.01);
(Continued)

(58) Field of Classification Search
CPC ...... A61J 11/0005; A61J 11/001; A61J 11/04; A61J 9/0638; A61J 9/0676; A61J 9/00;
(Continued)

(56) References Cited

U.S. PATENT DOCUMENTS

| 279,935 | A | * | 6/1883 | Glattsteine | ............... A61J 9/02 215/11.2 |
| 2,197,672 | A | * | 4/1940 | Winters | ............... B65D 47/305 222/490 |

(Continued)

FOREIGN PATENT DOCUMENTS

WO     20190173704     9/2019

OTHER PUBLICATIONS

International Search Report and Written Opinion for PCT/US20/70107, dated Sep. 23, 2020.
(Continued)

*Primary Examiner* — Gideon R Weinerth
(74) *Attorney, Agent, or Firm* — Womble Bond Dickinson (US) LLP

(57) ABSTRACT

The disclosure includes embodiments of an apparatus, a device, and methods to transform an infant feeding bottle into an infant gavage feeding apparatus. According to an embodiment, an infant gavage feeding apparatus can include an infant feeding bottle, a gavage milk delivery component, a retaining ring, and a cord component. In another embodiment, an infant milk dual-delivery device to transform an infant feeding bottle to an alternate nipple feeding and gavage feeding apparatus includes a gavage milk delivery component, a retaining ring, and a nipple receiving component. The gavage milk delivery component and the nipple receiving component can be positioned in a branched or a stacked configuration. The device can include a flow closure component and a controller to transition the milk flow for a gavage feeding and nipple feeding. The device can include a funnel to allow milk in the nipple to flow back into the infant feeding bottle.

5 Claims, 14 Drawing Sheets

Related U.S. Application Data

(60) Provisional application No. 62/640,346, filed on Mar. 8, 2018.

(51) Int. Cl.
| | |
|---|---|
| *A61M 39/00* | (2006.01) |
| *A61J 11/00* | (2006.01) |
| *A61J 7/00* | (2006.01) |
| *A61J 9/08* | (2006.01) |
| *A61J 11/04* | (2006.01) |
| *A61J 9/06* | (2006.01) |
| *B65D 1/02* | (2006.01) |
| *A61M 3/02* | (2006.01) |

(52) U.S. Cl.
CPC .............. *A61J 9/006* (2013.01); *A61J 9/0638* (2015.05); *A61J 9/0676* (2015.05); *A61J 9/085* (2013.01); *A61J 11/001* (2013.01); *A61J 11/04* (2013.01); *A61J 15/0003* (2013.01); *B65D 1/02* (2013.01); *A61J 15/0011* (2013.01); *A61M 3/0241* (2013.01)

(58) Field of Classification Search
CPC .......... A61J 9/006; A61J 9/085; A61J 7/0053; A61J 15/0003; A61J 11/00; A61J 15/00; A61J 15/0011; B65D 1/02; A61M 31/00; A61M 3/0241
USPC ......... 215/11.1, 388, 387, 400; 604/403, 27; 606/236; 251/310; 222/556, 481, 545, 222/546, 485, 566
See application file for complete search history.

(56) References Cited

U.S. PATENT DOCUMENTS

| | | | | | |
|---|---|---|---|---|---|
| 2,330,019 | A | * | 9/1943 | Vaughn | A61J 9/00 215/11.1 |
| 2,600,978 | A | | 6/1952 | Demarco, Jr. | |
| 2,968,262 | A | * | 1/1961 | Lacey | A23G 3/28 425/183 |
| 3,065,873 | A | * | 11/1962 | Plate | A61J 9/00 215/11.1 |
| 3,078,848 | A | * | 2/1963 | Milbert | A61M 3/0241 604/32 |
| 3,645,262 | A | | 2/1972 | Harrigan | |
| 3,797,486 | A | * | 3/1974 | Shaps | A61M 39/02 604/246 |
| 3,865,107 | A | | 2/1975 | Barton | |
| 3,990,597 | A | * | 11/1976 | Barton | B65D 51/1622 215/11.5 |
| 4,821,895 | A | * | 4/1989 | Roskilly | A61J 7/0053 215/390 |
| 4,898,290 | A | * | 2/1990 | Cueto | A61J 9/00 215/11.1 |
| 4,925,042 | A | * | 5/1990 | Chong | A61J 9/00 215/11.1 |
| 4,940,151 | A | * | 7/1990 | Fett | A61J 9/00 215/11.1 |
| 4,994,076 | A | * | 2/1991 | Guss | A61J 9/00 215/11.1 |
| 5,040,756 | A | * | 8/1991 | Via Cava | A61J 9/0661 248/103 |
| 5,049,127 | A | * | 9/1991 | Yen Tseng | A61J 15/0011 604/79 |
| 5,062,550 | A | * | 11/1991 | Singh | A23G 3/2023 222/80 |
| 5,421,496 | A | * | 6/1995 | Korsinsky | A61J 11/0005 215/11.1 |
| 5,443,453 | A | * | 8/1995 | Walker | A61M 39/223 137/625.41 |
| 5,466,228 | A | * | 11/1995 | Evans | A61M 39/223 137/625.47 |
| 5,489,075 | A | | 2/1996 | Ible | |
| 5,540,668 | A | * | 7/1996 | Wilson, Jr. | A61M 39/223 604/248 |
| D379,492 | S | * | 5/1997 | Walker | D23/233 |
| 5,653,353 | A | | 8/1997 | Otto et al. | |
| 5,749,483 | A | * | 5/1998 | Tebeau | A61J 9/00 215/11.1 |
| 5,794,819 | A | * | 8/1998 | Smith | B65D 47/30 220/525 |
| 6,280,422 | B1 | * | 8/2001 | Sanchez-Browning | A61M 5/14 137/845 |
| 6,302,286 | B1 | * | 10/2001 | Witherspoon | A61J 11/008 215/11.1 |
| 6,923,332 | B1 | * | 8/2005 | Thomas | A61J 9/00 215/11.1 |
| 7,172,085 | B2 | * | 2/2007 | Beaudette | A61J 9/00 215/11.1 |
| 7,282,044 | B2 | | 10/2007 | Hudson et al. | |
| 7,799,008 | B2 | | 9/2010 | Hendricks | |
| D642,260 | S | * | 7/2011 | Hendricks | A61J 9/00 D24/121 |
| 7,984,817 | B1 | * | 7/2011 | Everett | B65D 47/06 215/11.5 |
| 8,292,844 | B1 | * | 10/2012 | Diomede | A61M 31/00 604/82 |
| 9,296,531 | B2 | | 3/2016 | Luzbetak et al. | |
| 9,456,960 | B2 | | 10/2016 | Ginzburg et al. | |
| 9,884,148 | B2 | * | 2/2018 | Mehta | A61H 35/04 |
| 2003/0132185 | A1 | * | 7/2003 | Beaudette | A61J 9/006 215/11.4 |
| 2008/0103475 | A1 | * | 5/2008 | Hendricks | A61J 15/0096 604/403 |
| 2009/0247941 | A1 | * | 10/2009 | Lu | A61M 3/0262 604/73 |
| 2010/0072162 | A1 | | 3/2010 | Park | |
| 2011/0011819 | A1 | * | 1/2011 | Lee | A61J 9/006 215/11.5 |
| 2016/0114096 | A1 | * | 4/2016 | Mehta | A61H 35/04 604/192 |
| 2018/0312326 | A1 | * | 11/2018 | Haden | A61J 9/0661 |
| 2018/0360694 | A1 | | 12/2018 | Frisch et al. | |
| 2019/0282451 | A1 | * | 9/2019 | Hoch | A61J 11/001 |
| 2021/0315778 | A1 | * | 10/2021 | Kilinc | A61J 9/006 |

OTHER PUBLICATIONS

Innovative nurses like Erin Hoch create solutions to common problems, Loma Linda University Health, May 3, 2018.

International Search Report and Written Opinion for PCT/US19/21334, dated May 15, 2019.

Medela, Breast Milk Transfer Lid, 2020.

* cited by examiner

APPARATUS, DEVICE, AND METHOD FOR INFANT GAVAGE FEEDING

CROSS-REFERENCE TO RELATED APPLICATIONS

This application is a continuation-in-part of PCT Application No. PCT/US19/21334, filed Mar. 8, 2019, titled "APPARATUS, DEVICE, METHOD, AND KIT FOR INFANT GAVAGE FEEDING," which claims priority to, and the benefit of, U.S. Provisional Application No. 62/640,346, filed Mar. 8, 2018, titled "APPARATUS, DEVICE, METHOD, AND KIT FOR INFANT GAVAGE FEEDING," each of which is incorporated herein by reference in its entirety.

BACKGROUND

1. Field of Invention

The present disclosure relates generally to the field of infant gavage feeding and, more particularly, to an apparatus, a device, and methods to allow a standard infant feeding bottle to readily to convert into a gavage feeding device for facilitating the delivery of oral fluids such as milk to an infant.

2. Description of the Prior Art

Many babies struggle to breast or bottle feed, whether due to underdeveloped sucking and swallowing reflexes from being born prematurely or being otherwise too small or weak; due to coordination difficulties; as a result of throat, esophagus, or bowel issues; or from lung or heart problems, any of which may make standard breast or bottle feeding difficult, or in some cases impossible. Without the ability to breast or bottle feed, these babies are at risk of malnourishment absent other methods of feeding. Gavage feedings, using enteral feeding tubes, are often relied upon to supplement or replace breast or bottle feeding.

In some cases, babies may initially be bottle fed, but may require gavage feeding after a certain amount of milk or formula has been consumed orally. The process of switching from standard bottle feeding via a nipple to gavage feeding can be cumbersome, however, and can interrupt the flow and bonding of a feeding session. Currently, to achieve this difficult transition, any milk or formula remaining in the bottle is typically transferred from the original, standard bottle to another bottle and drawn up by a syringe from the secondary bottle, after which the syringe is attached to enteral tubing to deliver the milk directly to the baby's stomach. This process is unwieldy, and often necessitates putting the baby down or enlisting the help of a second person, thereby disrupting the baby's feeding experience.

Milk may also be wasted in the process, as a complete transfer of the remaining milk from the original bottle to the gavage feeding device is unlikely. This milk loss is wasteful and may create difficulties in tracking the exact volume of milk consumed by the baby. When gavage feeding, for example, there is a chance that when pouring the milk to gavage there might be spillage, resulting in loss of breast milk of unknown volume, particularly when a sole nurse or caregiver attempts to hold a wriggling baby during the bottle-to-gavage transfer process. To counteract this inevitable loss, many neonatal intensive care unit (NICU) facilities prepare more milk than needed, in order to compensate for breast milk that is wasted in the enteral tubing. Some mothers produce very small amounts of milk, such that any excess milk that is being made or wasted is likely detracting from the mother and baby's supply, or such that more donor milk is used than is necessary.

NICU facilities must also take into account that syringes, bottles, and pumps often do not have consistent and corresponding measurements. In some cases, if not measured correctly, any milk remaining in the enteral feeding tube at the completion of gavage feeding might be kept from the baby because, per the pump fluid measurements, the feeding may appear to be completed. As a result of this measuring inconsistency, the baby may have lost a portion of milk that was needed to meet total fluid nutritional requirements. With eight feeds per day, these repeated under-measurements could deprive the baby of substantial portions of necessary fluids and caloric needs.

SUMMARY

Applicant has recognized the difficulties noted above and that there is an unmet need for an apparatus, device, and method to efficiently convert a standard infant feeding bottle from nipple-delivered milk or formula feeding to gavage feeding, while avoiding the clumsiness and waste of typical transition methods. Applicant has also recognized that there is a need for an apparatus, device, and method to swap between nipple and gavage feeding easily. The present disclosure is directed to an apparatus, device, and method for infant gavage feeding that provides an elegant solution to these previously unmet needs.

According to an embodiment, an infant gavage feeding apparatus may include an infant feeding bottle, a gavage milk delivery component, a retaining ring, and a cord component. The infant feeding bottle may include a nipple secured to a top portion thereof in order to facilitate nipple feeding. The gavage milk delivery component may include a frustoconical portion. An elongate tube portion may be connected to and extend outwardly and distally from the frustoconical portion. The elongate tube portion may be positioned to connect with an enteral feeding tube when positioned adjacent thereto in order to facilitate gavage feeding. The retaining ring may be positioned to secure a base of the frustoconical portion of the gavage milk delivery component to the top portion of the infant feeding bottle. The cord component may be positioned to releasably connect the gavage milk delivery component to the infant feeding bottle in order to transition the infant feeding bottle from nipple feeding to gavage feeding.

In some embodiments, the nipple of the infant feeding bottle may be removable from the top portion of the infant feeding bottle so as to allow attachment of the retaining ring to the infant feeding bottle.

In some embodiments, the cord component may be positioned to releasably connect the gavage milk delivery component to the infant feeding bottle when the gavage milk delivery component is not in use. The cord component may be detachable from the gavage milk delivery component when the retaining ring is secured to the top portion of the infant feeding bottle, according to some embodiments.

In some embodiments, the cord component may further include a clip positioned thereon to secure the infant gavage feeding apparatus in an inverted orientation so as to allow hands-free feeding when the cord component has been detached from the gavage milk delivery component.

In some embodiments, the cord component may further include a grip component positioned at a proximal end of the cord so as to removably attach the cord component to the infant feeding bottle, the grip portion of the cord component being positioned to slidably move along a longitudinal axis of the infant feeding bottle after the cord component is detached from the gavage milk delivery component so as to allow the infant gavage apparatus to be stably supported when the infant gavage apparatus is in an inverted orientation.

In some embodiments, the apparatus may further include a releasable seal positioned at a bottom of the retaining ring, a perimeter of the releasable seal attached to a perimeter of the bottom of the retaining ring thereby sealing the bottom of the retaining ring so as to prevent contamination of an interior of the gavage milk delivery component when the gavage milk delivery component is not in use.

In some embodiments, the apparatus may further include a removable protective cap positioned to cover the gavage milk delivery component when the protective cap is affixed to the retaining ring so as to prevent contamination of the elongate tube portion of the gavage milk delivery component when the gavage milk delivery component is not in use.

The present disclosure also discloses embodiments directed to an infant milk dual-delivery device to transform an infant feeding bottle to an alternate nipple feeding and gavage feeding apparatus. In some embodiments, the device may include a nipple receiving component, a gavage milk delivery component, and a retaining ring. The nipple receiving component may be positioned to allow a nipple to be removably connected to the infant milk dual-delivery device in order to facilitate nipple feeding, according to an embodiment. The gavage milk delivery component may include a frustoconical portion, according to an embodiment. In an embodiment, an elongate tube portion may be connected to and extend outwardly and distally from the frustoconical portion. In an embodiment, the elongate tube portion may be positioned to connect with an enteral feeding tube when positioned adjacent thereto in order to facilitate gavage feeding. The retaining ring may be positioned to secure a base of the gavage milk delivery component to a top portion of the infant feeding bottle, according to an embodiment. In an embodiment, the nipple may be removable from the top portion of the infant feeding bottle in order to allow attachment of the retaining ring to the infant feeding bottle.

In some embodiments, the gavage milk delivery component and the nipple receiving component may be positioned in a branched configuration so that the configuration may position the infant milk dual-delivery device in a first position to enable gavage feeding via the gavage milk delivery component and position the infant milk dual-delivery device in a second position to enable nipple feeding via the nipple.

In some embodiments, the device may further include a flow closure component and a controller. The flow closure component may be positioned in order to divide a milk flow path from the infant feeding bottle into a first channel and a second channel. The first channel may include the milk flow path from the infant feeding bottle to the nipple, and the second channel may include the milk flow path from the infant feeding bottle to the gavage milk delivery component. The first channel may facilitate nipple feeding and the second channel may facilitate gavage feeding. The controller may be positioned to transition the flow closure component between a first position to facilitate nipple feeding via the first channel and a second position to facilitate gavage feeding via the second channel.

In another embodiment, the gavage milk delivery component and the nipple receiving component may be positioned in a stacked configuration in order to allow milk to flow through the gavage milk delivery component and the nipple when nipple feeding. The gavage milk delivery component and the nipple receiving component may be positioned in a stacked configuration in order to allow milk to flow through the gavage milk delivery component when the nipple is removed from the nipple receiving component in order to facilitate gavage feeding.

In some embodiments, the device may further include a funnel. The apex of the funnel may be insertable into a distal end of the elongate tube portion of the gavage milk delivery component. The base of the funnel may be positioned to circumvent a base of the nipple when positioned thereon in order to allow milk in the nipple to flow back into the infant feeding bottle through the elongate tube portion of the gavage milk delivery component when the infant feeding bottle is positioned in an upright position in order to avoid loss of milk.

In an embodiment, a flow closure component may be positioned so as to divide a milk flow path from the infant feeding bottle into a first channel and a second channel. In an embodiment, the first channel may include the milk flow path from the infant feeding bottle through an area circumventing an opening in the base of the gavage milk delivery component and into the nipple, and the second channel may include the milk flow path from the infant feeding bottle through the opening in the base of the gavage milk delivery component.

In an embodiment, the device may further include a removable protective cap positioned to cover the gavage milk delivery component when the flow closure component is positioned so as to divert milk along the first channel, so as to prevent contamination of the elongate tube portion of the gavage milk delivery component when the gavage milk delivery component is not in use.

The present disclosure further includes embodiments directed to a method to operate an infant gavage feeding apparatus. In some embodiments, for example, the method may include attaching a gavage milk delivery component to an infant feeding bottle. The cord component may be positioned to releasably connect the gavage milk delivery component to the infant feeding bottle when the gavage milk delivery component is not in use, according to an embodiment. In an embodiment, the gavage milk delivery component may include a frustoconical portion. According to an embodiment, an elongate tube portion may be connected to and extend outwardly and distally from the frustoconical portion. The elongate tube portion may be positioned to connect with an enteral feeding tube when positioned adjacent thereto in order to facilitate gavage feeding, according to an embodiment. In an embodiment, the method may also include removing a nipple from a top portion of the infant feeding bottle, replacing the removed nipple with the gavage milk delivery component, fluidly connecting a distal end of the elongate tube portion of the gavage milk delivery component to a proximal end of the enteral feeding tube, and inverting the infant feeding bottle to initiate a flow of milk from the infant feeding bottle into the enteral feeding tube via the gavage milk delivery component in order to facilitate gavage feeding.

In an embodiment, the method may further include attaching a retaining ring to the infant feeding bottle, the retaining ring securing a base of the frustoconical portion of the gavage milk delivery component to the top portion of the infant feeding bottle. According to an embodiment, the method may further include, prior to replacing the removed nipple with the gavage milk delivery component, removing a releasable seal from a bottom of the retaining ring to expose the base of the frustoconical portion of the gavage milk delivery component so as to allow the gavage milk delivery component to be fluidly connected to the infant feeding bottle, the releasable seal positioned at the bottom of the retaining ring, a perimeter of the releasable seal attached to a perimeter of the bottom of the retaining ring thereby sealing the bottom of the retaining ring so as to prevent contamination of an interior of the gavage milk delivery component.

According to an embodiment, the method may further include, prior to replacing the removed nipple with the gavage milk delivery component, removing a removable protective cap from the retaining ring to expose the elongate tube portion of the gavage milk delivery component so as to allow coupling of the elongate tube portion of the gavage milk delivery component to the enteral feeding tube when the removable protective cap is removed, the removable protective cap positioned to cover the gavage milk delivery component when the removable protective cap is affixed to the retaining ring so as to prevent contamination of the elongate tube portion.

According to an embodiment, the method may include attaching a grip component to the infant feeding bottle, the grip component being positioned at a proximal end of the cord component so as to secure the gavage milk delivery component, positioned at a distal end of the cord component, to the infant feeding bottle.

According to an embodiment, the method may further include attaching the retaining ring to the infant feeding bottle, thereby breaking the cord component when the retaining ring is attached to the infant feeding bottle so as to disconnect the gavage milk delivery component from the grip component.

According to an embodiment, the method may further include sliding the grip component of the cord component downwardly along a longitudinal axis of the infant feeding bottle after the cord component is detached from the gavage milk delivery component so as to allow the infant gavage feeding apparatus to be stably supported when the infant gavage feeding apparatus is in an inverted position.

According to an embodiment, the method may further include attaching a clip positioned on the cord component to a user to secure the infant gavage feeding apparatus in an inverted orientation so as to allow hands-free feeding.

The present disclosure further includes embodiments directed to a method to operate an alternate nipple feeding and gavage feeding apparatus. In some embodiments, the method may include removing a nipple from a top portion of an infant feeding bottle. The nipple may be removable from the top portion of the infant feeding bottle in order to allow attachment of an infant milk dual-delivery device to the top portion of the infant feeding bottle, according to an embodiment. The method may further include attaching the infant milk dual-delivery device to the top portion of the infant feeding bottle, according to an embodiment. In an embodiment, the infant milk dual-delivery device may include a gavage milk delivery component, a retaining ring, and a nipple receiving component. The gavage milk delivery component may include a frustoconical portion, according to an embodiment. According to an embodiment, an elongate tube portion may be connected to and extend outwardly and distally from the frustoconical portion. The elongate tube portion may be positioned to connect with an enteral feeding tube when positioned adjacent thereto in order to facilitate gavage feeding, according to an embodiment. In an embodiment, the retaining ring may be positioned to secure a base of the gavage milk delivery component to the top portion of the infant feeding bottle. According to an embodiment, the nipple receiving component may be positioned to allow the nipple to be removably connected to the infant milk dual-delivery device in order to facilitate nipple feeding. According to an embodiment, the gavage milk delivery component and the nipple receiving component may be positioned in a branched configuration in order to alternately facilitate nipple feeding and gavage feeding. The method may further include connecting the nipple to the nipple receiving component in order to facilitate nipple feeding and inverting the infant feeding bottle to initiate a flow of milk from the infant feeding bottle alternately into the nipple in order to facilitate nipple feeding and into the gavage milk delivery component in order to facilitate gavage feeding, according to an embodiment.

According to an embodiment, the method may further include positioning a flow closure component in a first position so as to facilitate nipple feeding, the flow closure component positioned so as to divide a milk flow path from the infant feeding bottle into a first channel and a second channel, the first channel forming the milk flow path from the infant feeding bottle to the nipple.

According to an embodiment, the method may further include positioning the flow closure component in a second position so as to facilitate gavage feeding, the second position opening the second channel forming the milk flow path from the infant feeding bottle to the gavage milk delivery component. According to an embodiment, the controller may be positioned to transition the flow closure component between the first position and the second position.

The present disclosure is also directed to a method to operate an alternate nipple and gavage feeding apparatus, and may include removing a nipple from a top portion of the infant feeding bottle, the nipple may be removable from the top portion of the infant feeding bottle in order to allow attachment of an infant milk dual-delivery device to the infant feeding bottle, and attaching the infant milk dual-delivery device to the top portion of the infant feeding bottle. The infant milk dual-delivery device may include a gavage milk delivery component, a retaining ring, and a nipple receiving component, according to an embodiment. The gavage milk delivery component may include a frustoconical portion, according to an embodiment. In an embodiment, an elongate tube portion may be connected to and extending outwardly and distally from the frustoconical portion. According to an embodiment, the elongate tube portion may be positioned to connect with an enteral feeding tube when positioned adjacent thereto in order to facilitate gavage feeding. The retaining ring may be positioned to secure a base of the gavage milk delivery component to the top portion of the infant feeding bottle, according to an embodiment. The nipple receiving component may be positioned to allow the nipple to be removably connected to the infant milk dual-delivery device in order to facilitate nipple feeding according to an embodiment. In an embodiment, the gavage milk delivery component and the nipple receiving component may be positioned in a stacked configuration in order to alternately facilitate nipple feeding and gavage feeding.

According to an embodiment, the method may further include inserting the apex of a funnel into a distal end of the elongate tube portion of the gavage milk delivery component, the base of the funnel being positioned to circumvent a base of the nipple when positioned thereon so as to allow milk in the nipple to flow back into the infant feeding bottle through the elongate tube portion of the gavage milk delivery component when the infant feeding bottle is positioned in an upright position so as to avoid loss of milk.

According to an embodiment, the method may further include connecting the nipple to the nipple receiving component so as to facilitate nipple feeding; inverting the infant feeding bottle to initiate a flow of milk from the infant feeding bottle into the nipple so as to facilitate nipple feeding; disconnecting the nipple from the nipple receiving component; removing the funnel from the gavage milk delivery component; fluidly connecting the distal end of the elongate tube portion of the gavage milk delivery component to a proximal end of the enteral feeding tube; and inverting the infant feeding bottle to initiate a flow of milk from the infant feeding bottle into the enteral feeding tube so as to facilitate gavage feeding.

According to an embodiment, the method may further include connecting the nipple to the nipple receiving component so as to facilitate nipple feeding; positioning a flow closure component in a first position to open a first channel so as to allow the milk to flow from the infant feeding bottle through an area circumventing an opening in the base of the gavage milk delivery component and into the nipple; inverting the infant feeding bottle to initiate the flow of milk from the infant feeding bottle into the nipple so as to facilitate nipple feeding; disconnecting the nipple from the nipple receiving component; fluidly connecting a distal end of the elongate tube portion of the gavage milk delivery component to a proximal end of the enteral feeding tube; positioning the flow closure in the second position to open a second channel so as to allow milk to flow from the infant feeding bottle through the opening in the base of the gavage milk delivery component; and inverting the infant feeding bottle to initiate the flow of milk from the infant feeding bottle into the enteral feeding tube so as to facilitate gavage feeding.

Other aspects and features of the present disclosure will become apparent to those of ordinary skill in the art after reading the detailed description herein and the accompanying figures.

BRIEF DESCRIPTION OF DRAWINGS

Some of the features and benefits of the present disclosure having been stated, others will become apparent as the description proceeds when taken in conjunction with the accompanying drawings, in which.

While the disclosure will be described in connection with the preferred embodiments, it will be understood that it is not intended to limit the disclosure to that embodiment. On the contrary, it is intended to cover all alternatives, modifications, and equivalents, as may be included within the spirit and scope of the disclosure as defined by the appended claims.

DETAILED DESCRIPTION

The foregoing aspects, features, and advantages of the present disclosure will be further appreciated when considered with reference to the following description of the following embodiments and accompanying drawings. In describing the following embodiments of the disclosure illustrated in the appended drawings, specific terminology will be used for the sake of clarity. The disclosure, however, is not intended to be limited to the specific terms used, and it is to be understood that each specific term includes equivalents that operate in a similar manner to accomplish a similar purpose. Numerous specific details, examples, and embodiments are set forth and described to provide a thorough understanding of various embodiments of the present invention. However, in certain instances, wellknown or conventional details are not described in order to provide a concise discussion of embodiments of the present disclosure.

When introducing elements of various embodiments of the present disclosure, the articles "a," "an," "the," and "said" are intended to mean that there are one or more of the elements. The terms "comprising," "including," and "having" are intended to be inclusive and mean that there may be additional elements other than the listed elements. Any examples of operating parameters and/or environmental conditions are not exclusive of other parameters/conditions of the disclosed embodiments. Additionally, it should be understood that references to "one embodiment," "an embodiment," "certain embodiments," or "other embodiments" of the present disclosure are not intended to be interpreted as excluding the existence of additional embodiments that also incorporate the recited features. Furthermore, reference to terms such as "above," "below," "upper," "lower," "side," "front," "back," or other terms regarding orientation are made with reference to the illustrated embodiments and are not intended to be limiting or exclude other orientations.

Figure 1:
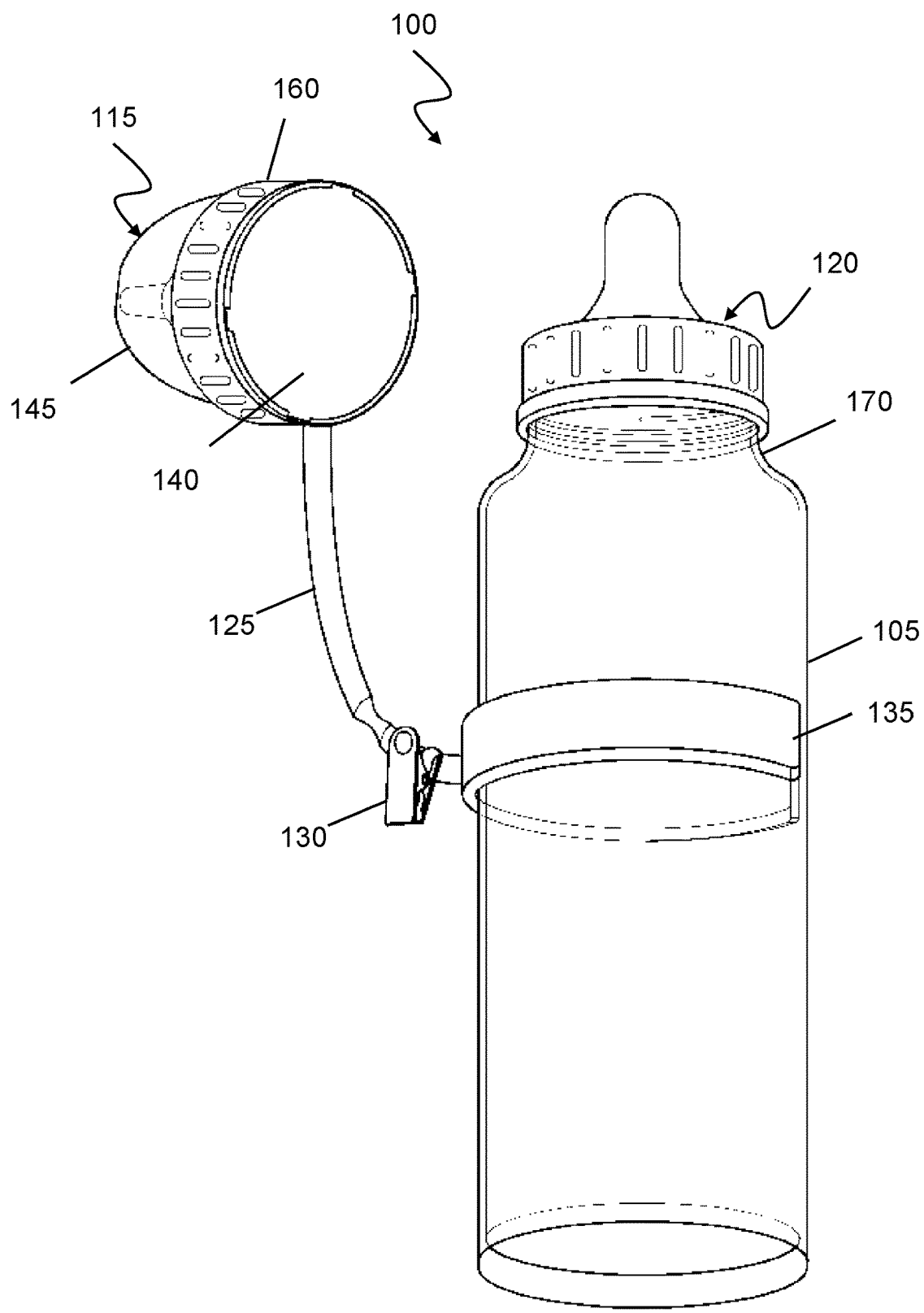
FIG. 1 is a perspective view of an infant gavage feeding apparatus having a gavage milk delivery component connected to an infant feeding bottle, according to an embodiment.

The present disclosure is directed to an infant gavage feeding apparatus 100, for example as illustrated in FIG. 1. The infant gavage feeding apparatus 100 can include an infant feeding bottle 105, a gavage milk delivery component 115, a retaining ring 160, and a cord component 125, according to an embodiment. The infant feeding bottle 105, for example, can be a standard or universal infant feeding bottle, which may be compatible with a variety of infant feeding nipples, depending on individual infant ages and other physiological needs. As further illustrated in the embodiment of FIG. 1, the nipple 120 of the infant feeding bottle 105 may be secured to the top portion 170 of the infant feeding bottle 105 in order to facilitate nipple feeding.

Figure 2:
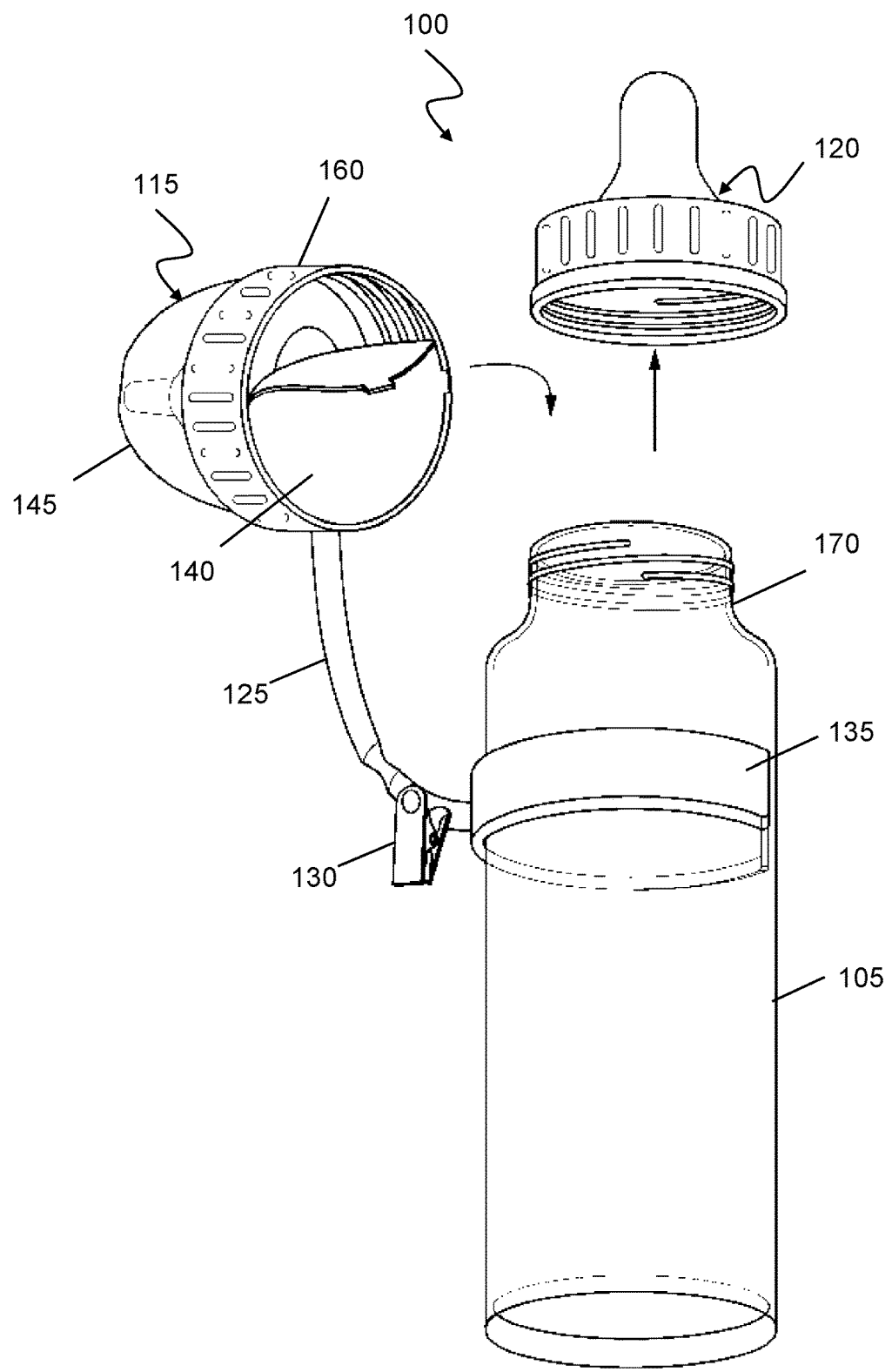
FIG. 2 is a perspective view of an infant gavage feeding apparatus having a nipple removed from an infant feeding bottle and a resealable seal partially removed from a bottom of a retaining ring of a gavage milk delivery component, according to an embodiment.

FIG. 2 illustrates a perspective view of an infant gavage feeding apparatus 100. As illustrated in FIG. 2, the nipple 120 of the infant feeding bottle 105 has been removed from the top portion 170 of the infant feeding bottle 105 in order to allow attachment of the gavage milk delivery component 115 and the retaining ring 160 to the top portion 170 of the infant feeding bottle 105.

Figure 4:
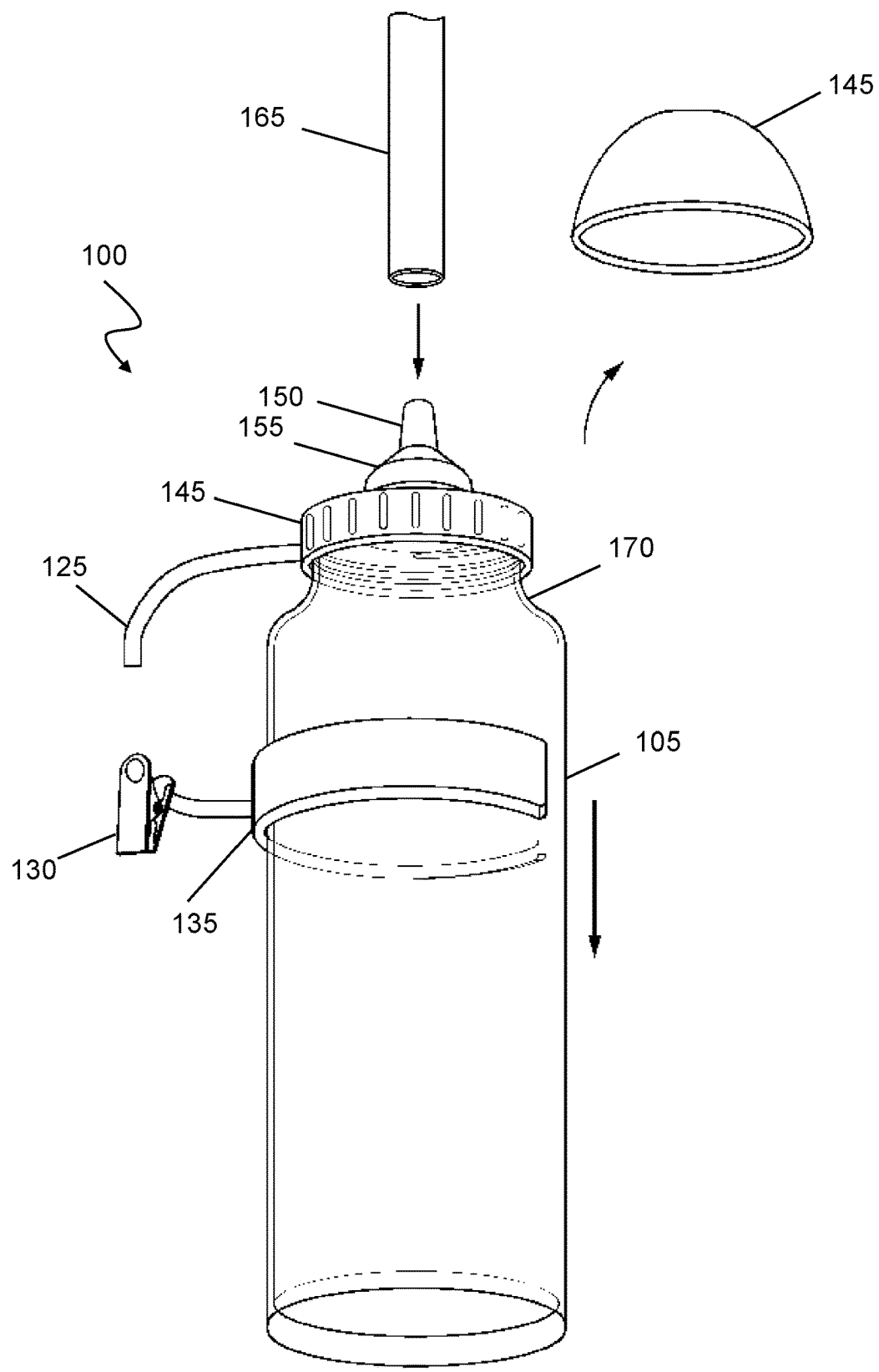
FIG. 4 is a perspective view of an infant gavage feeding apparatus, an enteral feeding tube, and a removable protective cap, according to an embodiment.

As illustrated in FIG. 4, the gavage milk delivery component 115 can include a frustoconical portion 155 having an elongate tube portion 150 connected to and extending outwardly and distally from the frustoconical portion 155. The elongate tube portion 150 can be positioned to connect with an enteral feeding tube 165 when positioned adjacent thereto, in order to facilitate gavage feeding, for example as further illustrated in FIG. 4.

In various embodiments, the enteral feeding tube 165 can be selected from any of a nasogastric (NG) tube, an orogastric (OG) tube, a nasoduodenal (ND) tube, a nasojejunal (NJ) tube, a gastric or gastrostomy (G) tube, a gastrojejunal (GJ) tube, a transjejunal tube, and a jejunal (J) tube, or any other enteral feeding tube as will be readily understood by one having ordinary skill in the art. In addition, in various embodiments the elongate tube portion 150 of the milk delivery component 115 can connect or connect to the enteral feeding tube 165 by any means understood and utilized in the art, such as by a threaded or snap connection, or by simple male-to-female insertion, among others, as will be readily understood by one having ordinary skill in the art.

In some embodiments, for example, the frustoconical portion 155 and elongate tube portion 150 of the gavage milk delivery component 115 can be formed of molded plastic having varying diameters for each portion formed in a stepwise sequence, as illustrated. In other embodiments, the frustoconical portion 155 and elongate tube portion 150 of the gavage milk delivery component 115 can be formed such that the transition between each segment is gradual or continuous. In other embodiments, the frustoconical portion 155 and elongate tube portion 150 can be formed as a single, continuous component, formed of the same molded plastic, rubber, silicone, or other appropriate material, as will be readily understood by one of ordinary skill in the art.

In some other embodiments, for example, the frustoconical portion 155 and elongate tube portion 150 of the milk delivery component 115 can be formed of plastic or some other suitable solid or semi-solid material to facilitate flow of milk or formula from the infant feeding bottle 105 to the enteral feeding tube 165, and to allow for secure coupling between the elongate tube portion 150 and the enteral feeding tube 165. In some embodiments, the milk delivery component 115 and/or the infant gavage feeding device 150 may be formed of bisphenol-a (BPA)-free plastic. Appropriate materials for formation of the milk delivery component 115 and the infant gavage feeding device 150 will be readily understood by one of ordinary skill in the art.

Returning to FIG. 1, the infant gavage feeding apparatus 100 can include a retaining ring 160 to secure a base of the frustoconical portion 155 of the gavage milk delivery component 115 to the top portion 170 of the infant feeding bottle 105. In some embodiments, for example, the retaining ring 160 can include a threaded component on an inner surface thereof for connecting the retaining ring 160 to the infant feeding bottle 105 in order to form a liquid-tight seal. In some other embodiments, various other attachment means between the retaining ring 160 and the top portion 170 of the infant feeding bottle 105 can be utilized, such as a snap fitting or the like, as will be readily understood by one of ordinary skill in the art.

As further illustrated in FIG. 2, the infant gavage feeding apparatus 100 can additionally include a cord component 125 to releasably connect the gavage milk delivery component 115 to the infant feeding bottle 105 in order to transition the infant feeding bottle 105 from nipple feeding to gavage feeding.

According to an embodiment of the present disclosure, the nipple 120 of the infant feeding bottle 105 may be removed from the top portion 170 of the infant feeding bottle 105 in order to allow attachment of the retaining ring 160 to the infant feeding bottle 105, as illustrated in FIG. 2 for example.

In some embodiments, for example, the cord component 125 may be positioned to releasably connect the gavage milk delivery component 115 to the infant feeding bottle 105 when the gavage milk delivery component 115 is not in use. In addition, the cord component 125 may be detachable from the gavage milk delivery component 115 when the retaining ring 160 is secured to the top portion 170 of the infant feeding bottle 105. In some embodiments, the cord component 125 may be made of plastic or like materials. In some embodiments, the cord component 125 may be designed to be reusable and for multiple uses. In various embodiments, the cord component 125 may include a breaking point positioned thereon at an appropriate location. The breaking point can allow the cord component 125 to disconnect into two separate components when sufficient force is applied on the cord component 125 to allow the cord component 125 to be detached from the gavage milk delivery component 115. The separated portions of the cord component 125 may be connected at the breaking point by any means understood and utilized in the art, such as by a magnetic, snap on, or male-to-female insertion, among others, as will be readily understood by one having ordinary skill in the art. In other embodiments, the breaking point can include a thinner portion of the material from which the cord component 125 is formed, such that the strength of the breaking point is weaker than that of the remainder of the cord component 125. As pressure is applied to the cord component 125, the weaker breaking point can detach.

In the embodiment illustrated in FIG. 4, for example, the cord component 125 may include a clip 130 positioned thereon to secure the infant gavage feeding apparatus 100 in an inverted orientation, for example to a caregiver, to an intravenous pole, to a piece of furniture, or the like, in order to allow hands-free feeding when the cord component 125 has been detached from the gavage milk delivery component 115.

Figure 5:
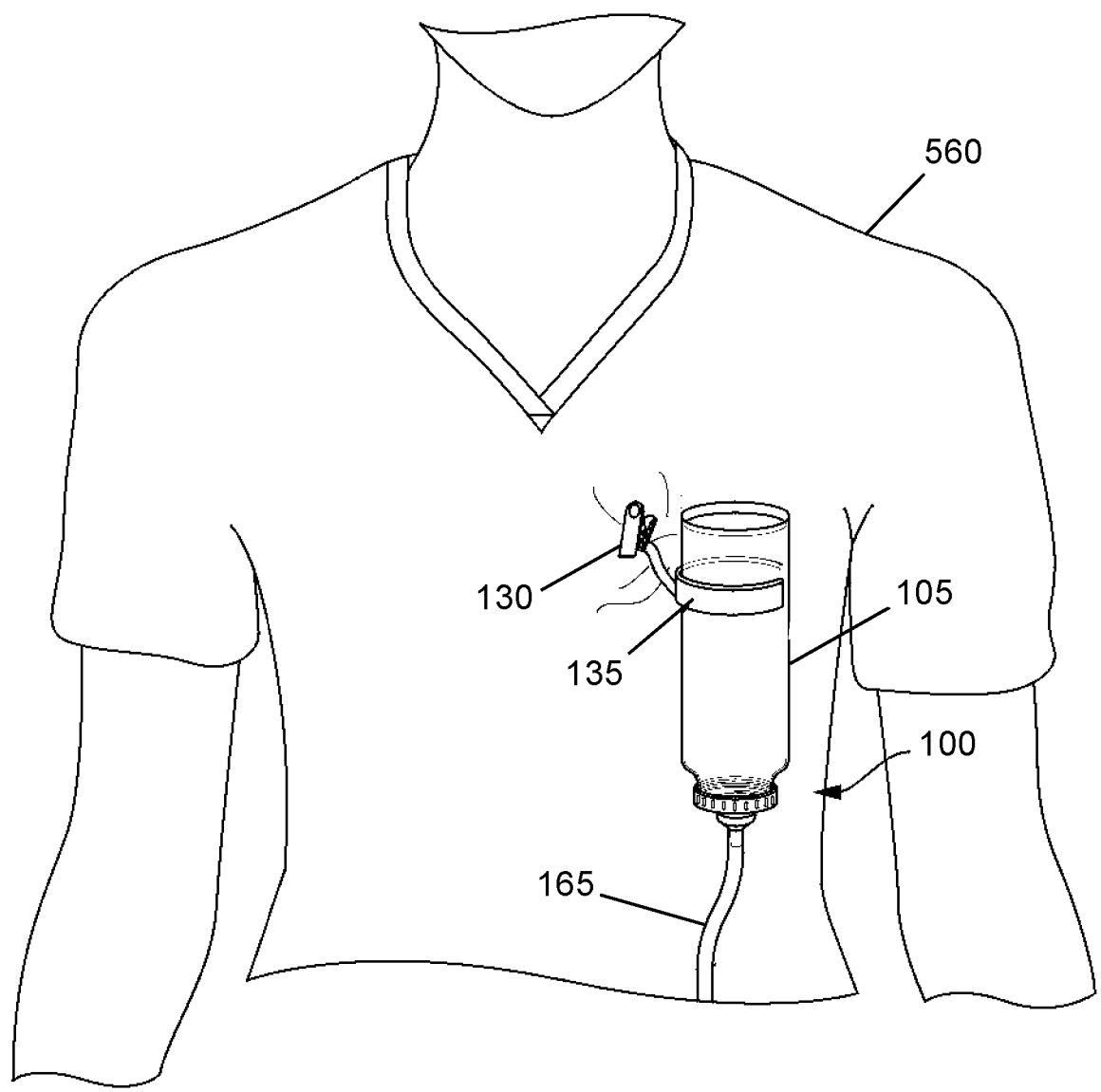
FIG. 5 is a partial front elevational view of a clip, a grip component, and an infant gavage feeding apparatus in use, according to an embodiment.

As further illustrated in FIG. 4, the cord component 125 can further include a grip component 135 positioned at a proximal end of the cord component 125 in order to removably attach the cord component 125 to the infant feeding bottle 105. In an embodiment, the grip component 135 of the cord component can 125 be positioned to slidably move along a longitudinal axis of the infant feeding bottle 105 after the cord component 125 is detached from the gavage milk delivery component 115 in order to allow the infant gavage apparatus 100 to be stably supported when the infant gavage apparatus 100 is in an inverted orientation, as illustrated in FIG. 5. The grip component 135 can include one or more ring structures to partially or fully encircle and removably secure the gavage milk delivery component 115 to the infant feeding bottle 105. In other embodiments, various other removable grip component means are contemplated, as will be readily understood by one of ordinary skill in the art.

In some embodiments, for example as illustrated in FIG. 2, the infant gavage feeding apparatus 100 can further include a releasable seal 140 positioned at a bottom of the retaining ring 160. In an embodiment, a perimeter of the releasable seal 140 is attached to a perimeter of the bottom of the retaining ring 160 thereby sealing the bottom of the retaining ring 160 in order to prevent contamination of an interior of the gavage milk delivery component 115 when the gavage milk delivery component 115 is not in use. The releasable seal 140 can be made from polymer materials such as polystyrene or polyethylene, among others, or can be a plastic or foil cover, as will be readily understood by one having ordinary skill in the art. The resealable seal 140 can be positioned to create a durable seal for repeat use in some examples, or can be disposable after a single use in other examples, and can be ergonomically easy to lift and peel away from the bottom of the retaining ring 160.

As illustrated in FIG. 4, the infant gavage feeding apparatus 100 can further include a removable protective cap 145 positioned to cover the gavage milk delivery component 115 when the protective cap 145 is affixed to the retaining ring 160, in order to prevent contamination of the elongate tube portion 150 of the gavage milk delivery component 115 when the gavage milk delivery component 115 is not in use. By way of example, the removable protective cap 145 can include a hemispherical dome cap or a cylindrical cap, among others, as will be readily understood by one having ordinary skill in the art. The removable protective cap 145 can be formed of opaque, translucent, or transparent medical-grade material. The removable protective cap 145 can connect to the retaining ring 160 by means of a snap-fitting connection, by a threaded connection, or by any other means as will be readily understood by one of ordinary skill in the art.

In some embodiments, the gavage milk delivery component 115 can further include a shoulder portion connected to and positioned between the base of the frustoconical portion 155 and the retaining ring 160. The shoulder portion can be positioned and angled so as to allow a flow of milk from the infant feeding bottle 105 into the enteral feeding tube 165 via the gavage milk delivery component 115. The angle at which the shoulder portion transitions between the base of the frustoconical portion 155 and the retaining ring 160 can help to prevent backup of the flow of milk from the infant feeding bottle 105 into the enteral feeding tube 165, as will be readily understood by one of ordinary skill in the art.

The present disclosure is also directed to an infant milk dual-delivery device 200 to transform an infant feeding bottle 105 to an alternate nipple feeding and gavage feeding apparatus. In some embodiments, the infant milk dual-delivery device 200 can be disposable after a single use. In other embodiments, infant the milk dual-delivery device 200 can be cleaned and sterilized between uses for reuse. The device 200, for example, can be fabricated from a variety of materials, including, but not limited to, common non-toxic and resilient polymeric materials, such as polyethylene or polyterephthalate, which are the preferred materials for infant feeding. In addition, the device 200 may be formed of medical-grade, lightweight, and highly durable thermal shock-resistant borosilicate glass, among others, as will be readily understood by one having ordinary skill in the art. The device 200 can also include other sturdy materials that are potentially easy to clean and sterilize.

Figure 6:
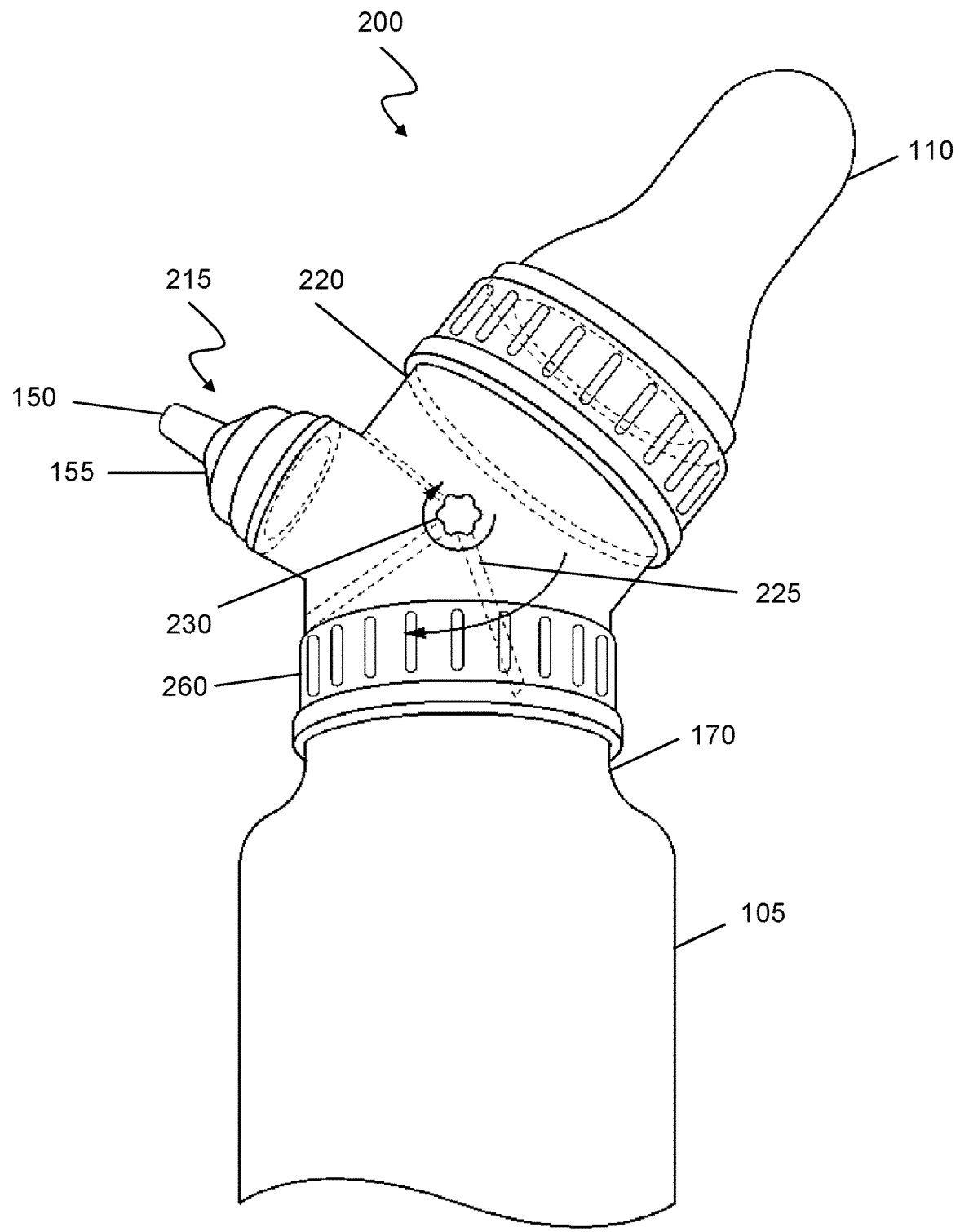
FIG. 6 is a partial perspective view of an infant milk dual-delivery device in a branched configuration connected to an infant feeding bottle and having a flow closure component in a position to facilitate nipple feeding, according to an embodiment.
Figure 7:
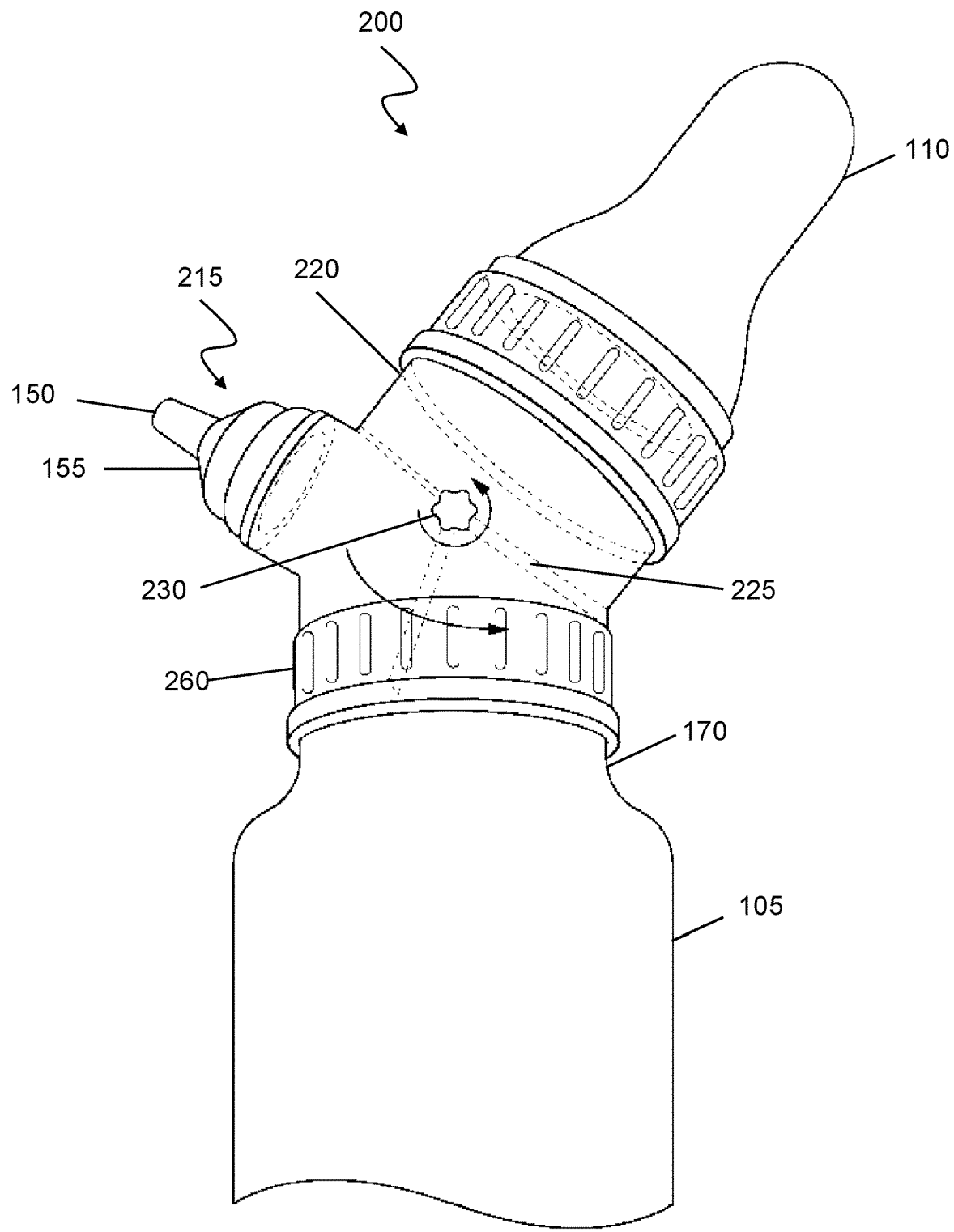
FIG. 7 is a partial perspective view of an infant milk dual-delivery device in a branched configuration connected to an infant feeding bottle and having a flow closure component in a position to facilitate gavage feeding, according to an embodiment.

In one or more embodiments, for example as illustrated in FIGS. 6 and 7, the device can include a nipple receiving component 220, a gavage milk delivery component 215, and a retaining ring 260. In some embodiments, the nipple receiving component 220 can be positioned to allow the nipple 110 to be removably connected to the infant milk dual-delivery device 200 in order to facilitate nipple feeding. In various embodiments, the nipple receiving component 220 can include a threaded component along an outer perimeter thereof for connecting the nipple 110 to the nipple receiving component 220 in order to form a liquid-tight seal. In other embodiments, various other attachment means between the nipple 110 and the nipple receiving component 220 may be utilized, such as a snap fitting or the like, as will be readily understood by one of ordinary skill in the art.

According to an embodiment of the present disclosure, the gavage milk delivery component 215 can include a frustoconical portion 155 and an elongate tube portion 150 connected to and extending outwardly and distally from the frustoconical portion 155. The elongate tube portion 150 can be positioned to connect with an enteral feeding tube 165 when positioned adjacent thereto in order to facilitate gavage feeding.

As illustrated in FIG. 7, the retaining ring 260 can be positioned to secure a base of the gavage milk delivery component 215 to a top portion 170 of an infant feeding bottle 105. The nipple 120 of the infant feeding bottle 105 is removable from the top portion 170 of the infant feeding bottle 105 in order to allow attachment of the retaining ring 260 to the infant feeding bottle 105.

In various embodiments, the base of the gavage milk delivery component 215 can be secured to the top portion 170 of the infant feeding bottle 105 via various attachment means such as a snap fitting. In another embodiment, the retaining ring 261 can include a threaded component encircling an outer portion thereof for connecting the retaining ring 261 to the top portion 170 of the infant feeding bottle 105. In other embodiments, various other attachment means between the retaining ring 260 and the top portion 170 of the infant feeding bottle 105 may be utilized, such as a snap fitting or the like, as will be readily understood by one of ordinary skill in the art.

The nipple receiving component 220 may be substantially cylindrical and tubular in shape to fit into the bottom of an existing and commercially available nipple receiving portion 120. In this way, a standard infant feeding bottle 105 and a standard nipple 110 can be utilized with the infant milk dual-delivery device 200 so as to convert a standard nipple-feeding bottle to a dual-delivery bottle capable of alternate nipple and gavage feedings, without requiring removal of the nipple when transitioning to gavage feeding. This configuration allows for seamless transitions between nipple and gavage feeding, so as to limit any interruption or unsettling of the baby's feeding process.

In the embodiments as illustrated in FIGS. 6 and 7, for example, the gavage milk delivery component 215 and the nipple receiving component 220 may be positioned in a branched configuration. The infant milk dual-delivery device 200 can be positioned in a first position, in which the nipple 110 is pointed downward and the gavage milk delivery component 215 is positioned upward, so as to enable nipple feeding via the nipple 110. In the first position, milk in the infant feeding bottle 105 will be allowed to flow by gravity into the nipple 110, without entering the elevated gavage milk delivery component 215. The infant milk dual-delivery device 200 may also be rotated to be positioned in a second position, in which the gavage milk delivery component 215 is positioned to point downward while the nipple 110 is pointed upward, so as to enable gavage feeding via the gavage milk delivery component 215. In the second position, milk in the infant feeding bottle 105 will be allowed to flow by gravity into the gavage milk delivery component 215, without entering the elevated nipple 110. In this way, a seamless transition between nipple and gavage feeding can be achieved.

In another embodiment, the infant milk dual-delivery device 205 can also include a flow closure component 225 and a controller 230. The flow closure component 225 can be positioned in order to divide a milk flow path from the infant feeding bottle 105 into a first channel and a second channel. The first channel can include the milk flow path from the infant feeding bottle 105 to the 110 nipple, and the second channel may include the milk flow path from the infant feeding bottle 105 to the gavage milk delivery component 215. The first channel may facilitate nipple feeding and the second channel may facilitate gavage feeding. In some embodiments, the flow closure component 225, for example, can be a cap, flap, tab, or the like, made of an impermeable material and appropriate dimension to complement the dimension of the interstitial space formed between the outer surfaces of the nipple receiving component 220 and the gavage milk delivery component 215 of the infant milk dual-delivery device 200, or any other suitable component positioned to block the first channel and prevent liquid, such as milk, from flowing into the first channel to facilitate nipple feeding.

In some embodiments, the controller 230 can be positioned to transition the flow closure component 225 between a first position to facilitate nipple feeding via the first channel and a second position to facilitate gavage feeding via the second channel. In some embodiments, the controller can include any controlling means to transition the flow closure component between a first position and a second position, such as a knob, a button, a handle, or a crown, among others, as will be readily understood by one having ordinary skill in the art. The controller 230 can be ergonomically designed and varied in size, shape, and materials. The controller 230, for example, can also be externally threaded or grooved for ease of grip while operating the controller, as will be readily understood by one having ordinary skill in the art. The controller 230 can be actuated by exerting sufficient force, such as by a rotation, sliding, or the like, to cause the flow closure component 225 to open the first channel and allow milk to flow from the infant feeding bottle 105 into the nipple 110. Similarly, the controller 230 can be actuated by exerting sufficient force, such as by a rotation, sliding, or the like, to cause the flow closure component 225 to open the second channel and allow milk to flow from the infant feeding bottle 105 into the gavage milk delivery component 215.

Figure 8:
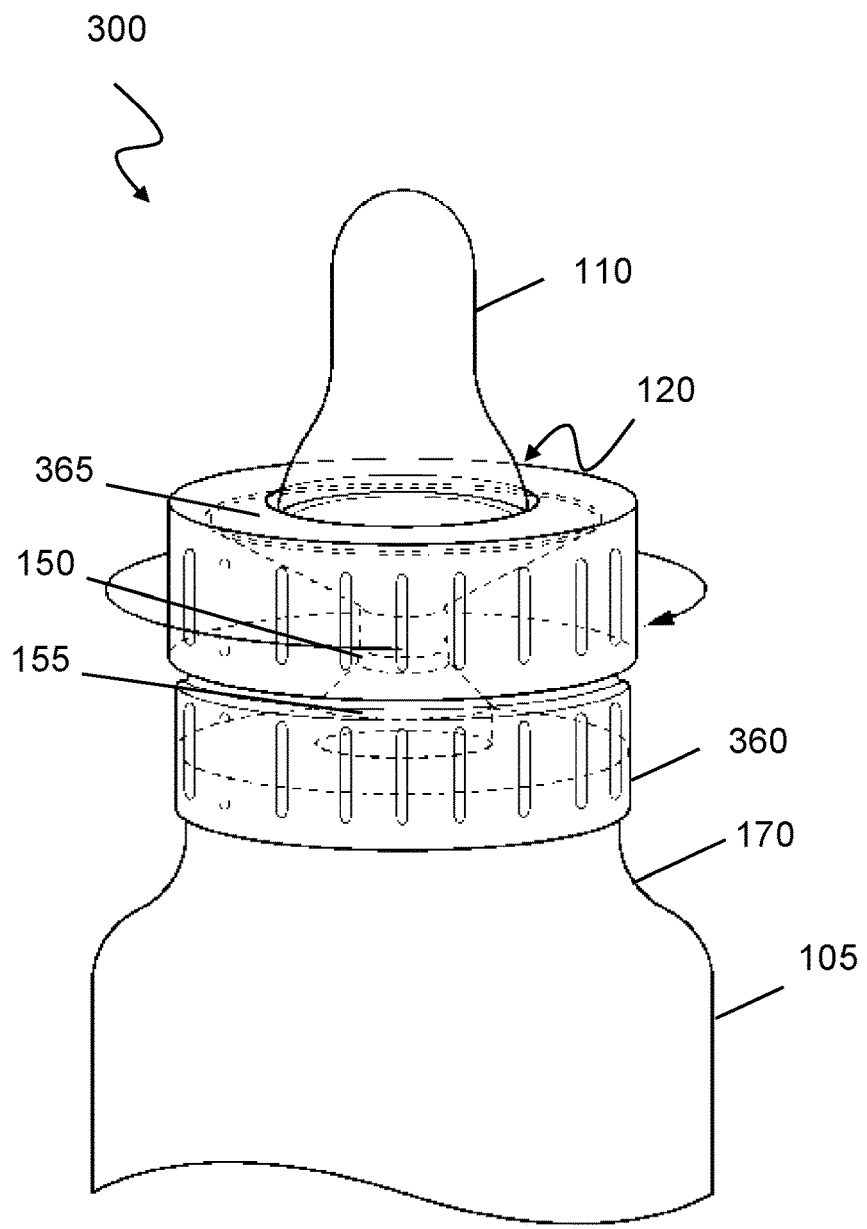
FIG. 8 is a partial perspective view of an infant milk dual-delivery device showing a gavage milk delivery component and a nipple receiving component in a stacked configuration, according to an embodiment.

In another embodiment of the infant milk dual-delivery device 300 as illustrated in FIG. 8, the gavage milk delivery component 315 and the nipple receiving component 320 can be positioned in series, in a stacked configuration in order to allow milk to flow through the gavage milk delivery component 315 and the nipple 110 when nipple feeding. Similarly, the stacked configuration can allow milk to flow through the gavage milk delivery component 315 when the nipple 110 is removed from the nipple receiving component 320 in order to facilitate gavage feeding. According to an embodiment, the gavage milk delivery component 315 and the nipple receiving component 320, for example, can be formed as a single and lightweight structure in that they are inseparable portions of an integrally formed structure, as will be readily understood by one of ordinary skill in the art.

In some embodiments, the upper portion of the nipple receiving component 320 may include a threaded component positioned on an outer surface thereof for receiving and connecting the nipple 120 to the nipple receiving component 320 in order to form a liquid-tight seal. In various embodiments, the nipple 120 can be connected to the nipple receiving component 320 by any means understood and utilized in the art, such as by a threaded or snap connection.

Figure 9:
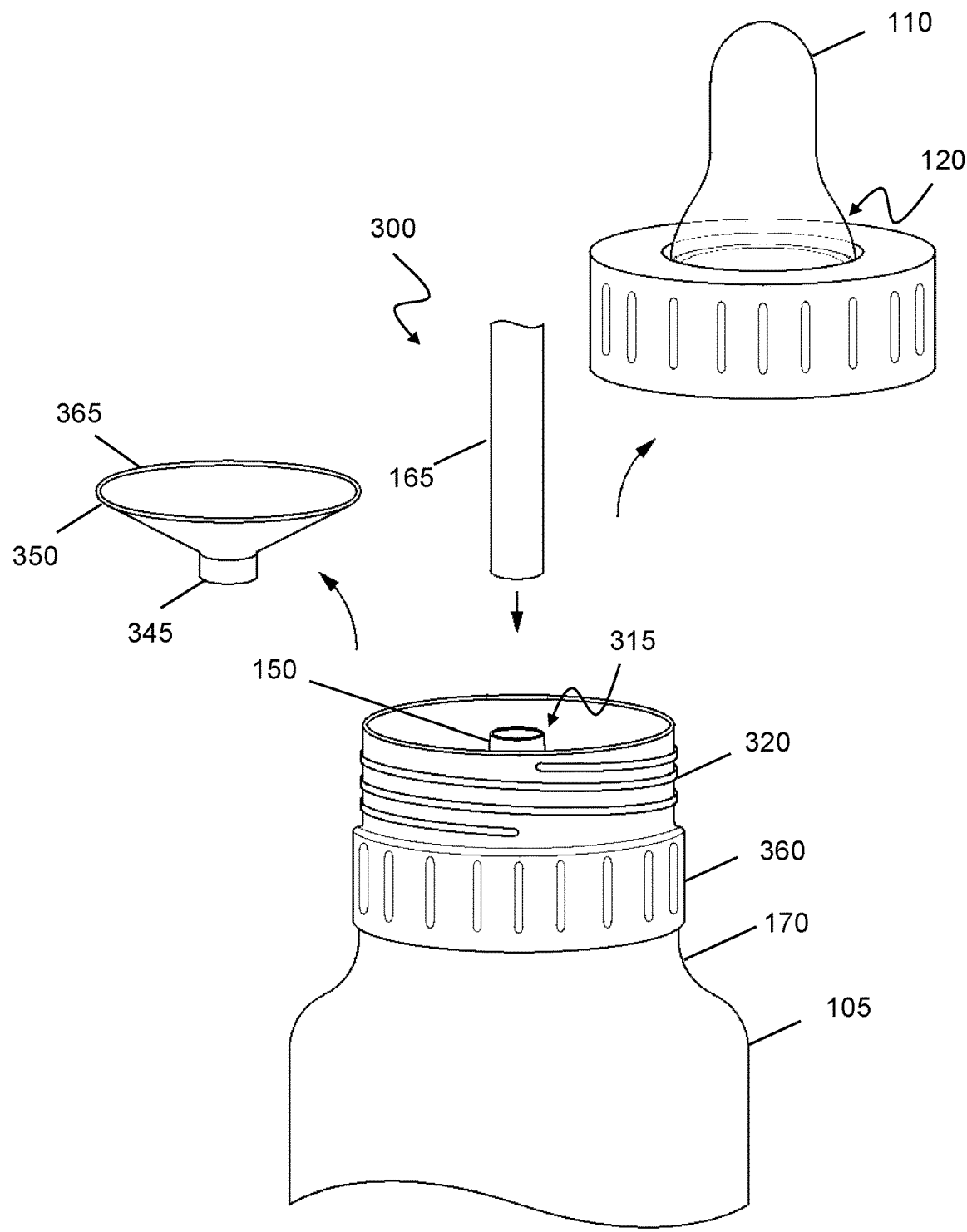
FIG. 9 is a partial perspective view of an infant milk dual-delivery device in a stacked configuration, a nipple, an enteral feeding tube, and a funnel, according to an embodiment.

As illustrated in FIG. 9, for example, the infant milk dual-delivery device 300 can further include a funnel 365. The apex 345 of the funnel 365 can include an elongated portion that is complementary to and insertable into a distal end of the elongate tube portion 150 of the gavage milk delivery component 315. In an embodiment, the base 350 of the funnel 365 can be positioned to circumvent a base of the nipple 110 when positioned thereon in order to allow milk in the nipple 110 to flow back into the infant feeding bottle 105 through the elongate tube portion 150 of the gavage milk delivery component 315 when the infant feeding bottle 105 is positioned in an upright position in order to avoid loss of milk. For example, milk may flow through the gavage milk delivery component 315 into the nipple 110 when the infant feeding bottle 110 is in an inverted position. When the infant feeding bottle 110 is rotated to an upright position, any milk remaining in the nipple 110 that has not been drained from the nipple by the baby will flow back downward toward the gavage milk delivery component 315. In the absence of the funnel 365, the milk may be trapped around the interstitial space formed between the elongate tube portion of the gavage milk delivery component 315 and the nipple receiving component 320. With the presence of the funnel 365, however, the milk may be directed to flow back through the gavage milk delivery component 315 and into the infant feeding bottle 105. In this way, loss of milk can be avoided.

The funnel 365, for example, can be formed of medical-grade and non-toxic sheet or film plastic, such as polyethylene or the like, as will be readily understood by one having ordinary skill in the art.

In some embodiments, the enteral feeding tube 165 can be inserted into a distal end of the elongate tube portion 150 of the gavage milk delivery component 315 when the funnel 365 is removed from the gavage milk delivery component 315 in order to facilitate gavage feeding, as illustrated in FIG. 9, for example.

Figure 12:
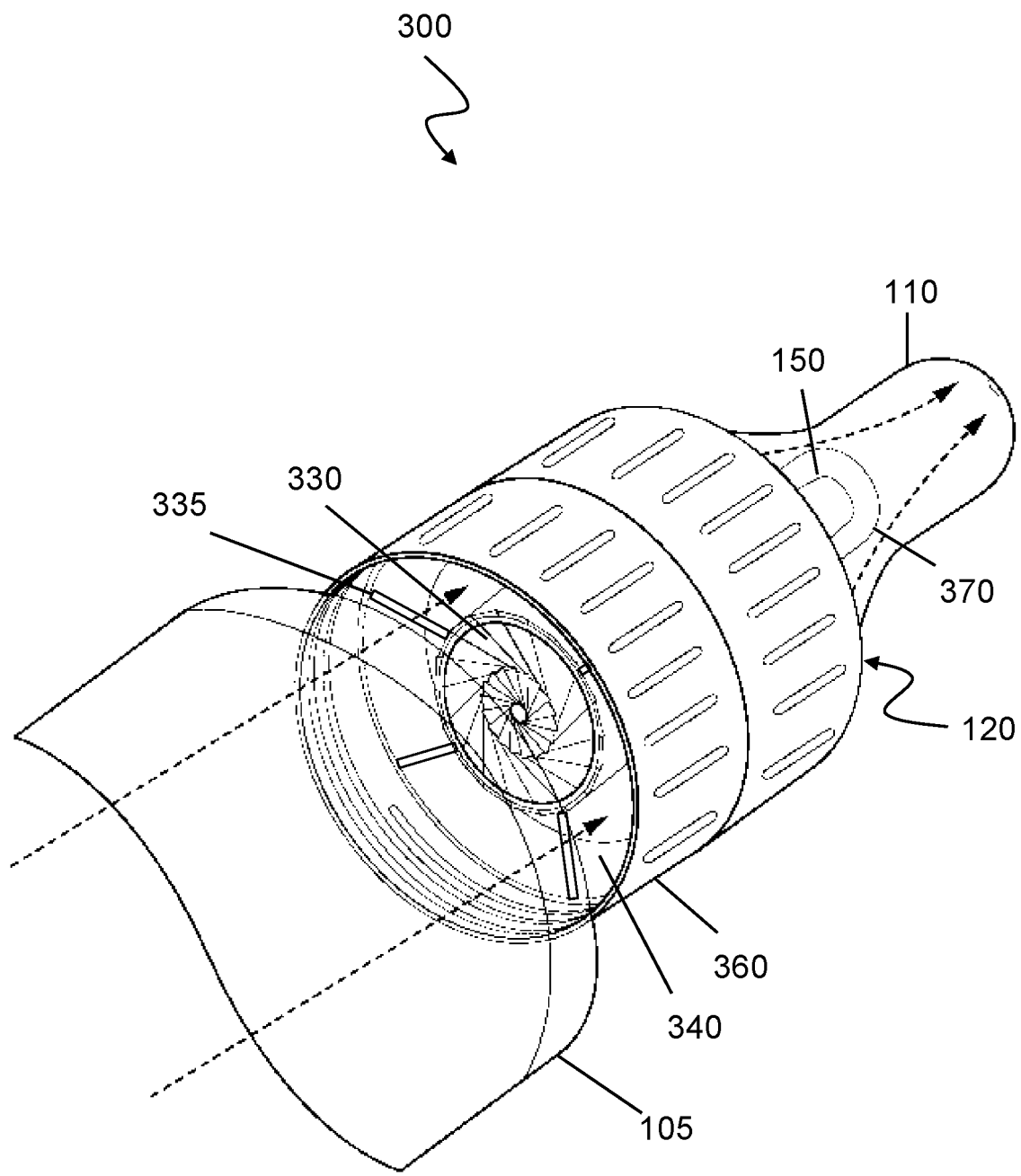
FIG. 12 is a partial rear perspective view of an infant milk dual-delivery device in a stacked configuration and having a flow closure component covering an opening in the base of the gavage milk delivery component to allow milk to flow through an area circumventing an opening in the base of the gavage milk delivery component and into the nipple, according to an embodiment.

As illustrated in FIG. 12, the infant milk dual-delivery device 300 can further include a flow closure component 330 positioned to divide a milk flow path from the infant feeding bottle 105 into a first channel and a second channel. The first channel can include the milk flow path from the infant feeding bottle 105 through an area circumventing an opening 340 in the base of the gavage milk delivery component 315 and into the nipple 110. The second channel can include the milk flow path from the infant feeding bottle 105 through the opening 310 in the base of the gavage milk delivery component 315. The gavage milk delivery component 315 can be attached to the retaining ring 360 by a plurality of supporting components 335 positioned around an outer perimeter of the gavage milk delivery component 315 in order to secure the gavage milk delivery component 315 to the retaining ring 360, while still allowing milk to flow along the first channel in the through an area circumventing an opening 340 in the base of the gavage milk delivery component 315 and into the nipple 110.

Figure 13:
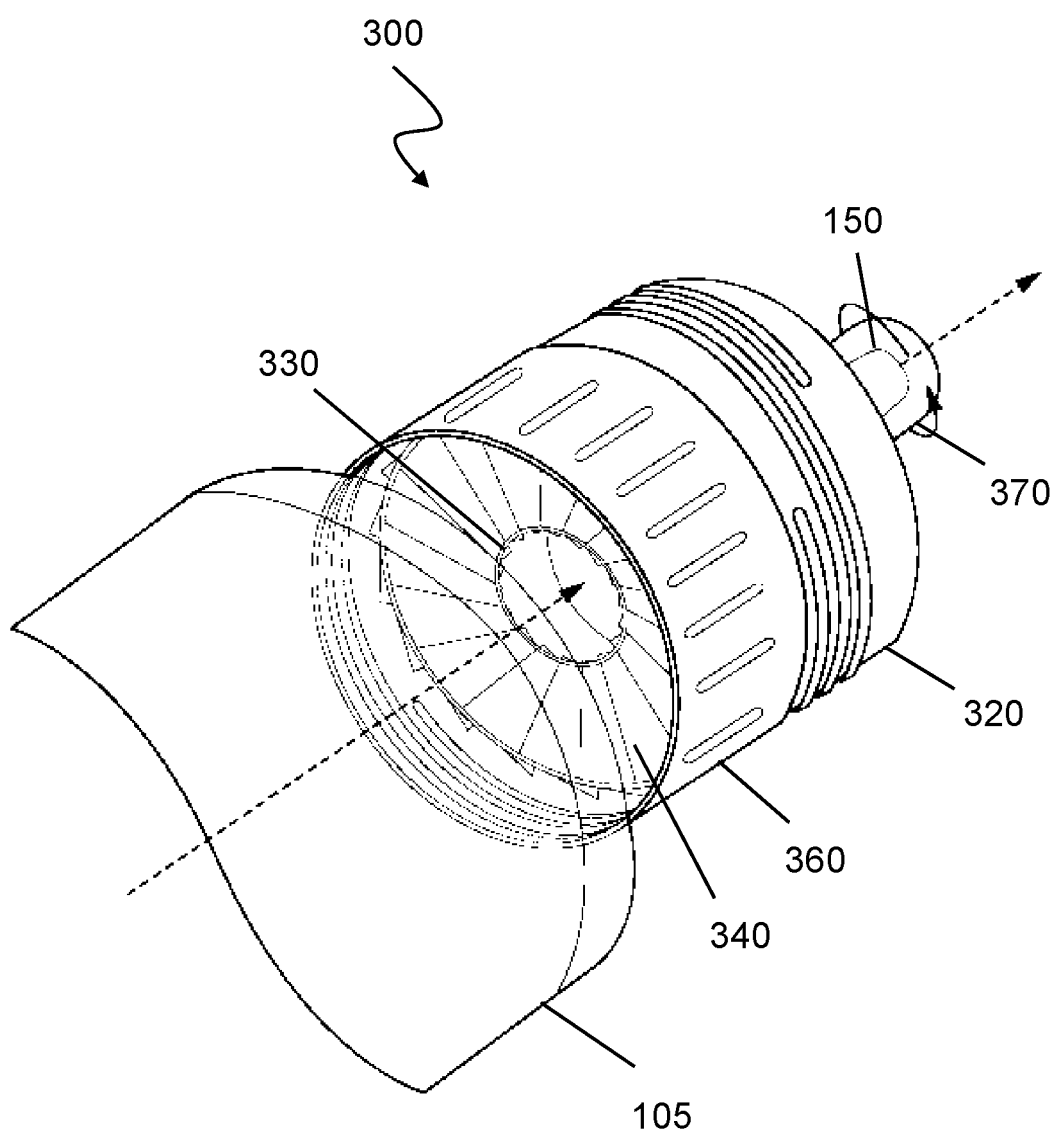
FIG. 13 is a partial rear perspective view of an infant milk dual-delivery device in a stacked configuration showing a flow closure component covering an area circumventing an opening in the base of the gavage milk delivery component and exposing an opening in the base of the gavage milk delivery component to facilitate gavage feeding, according to an embodiment.

In some embodiments, the flow closure component 330 can include a plurality of moveable overlapping covers that fit together in a circular arrangement. As illustrated in FIG. 13, milk flows from the infant feeding bottle 105 through the gavage milk delivery component 315 when the flow closure component covers an area 340 circumventing an opening 310 in the base of the gavage milk delivery component 315 and exposes the opening 310 in the base of the gavage milk delivery component 315.

In another embodiment, milk flows from the infant feeding bottle 105 through an area 340 circumventing an opening 310 in the base of the gavage milk delivery component 315 and into the nipple 110 when the flow closure component covers the opening 310 in the base of the gavage milk delivery component 315 and exposes the area 340 circumventing an opening 310 in the base of the gavage milk delivery component 315. In other embodiments, various other means of alternately covering the base of the gavage milk delivery component 315 and exposing the area 340 circumventing the opening 310 in the base of the gavage milk delivery component 315, and uncovering the base of the gavage milk delivery component 315 while covering the area 340 circumventing the opening 310 in the base of the gavage milk delivery component 315 may be used, such as rotating or sliding covers, flaps, or closures, as will be readily understood by one of ordinary skill in the art.

In the embodiments illustrated in FIGS. 12 and 13, the infant milk dual-delivery device 300 can further include a removable protective cap 370 positioned to cover the gavage milk delivery component 315 when the flow closure component 330 is positioned in order to divert milk along the first channel. The removable protective cap 370 can also be positioned to prevent contamination of the elongate tube portion 150 of the gavage milk delivery component 315 when the gavage milk delivery component 315 is not in use.

Additionally, the removable protective cap 370, for example, can be connected to the flow closure component 330 in order to cause the movement of the plurality of moveable overlapping covers and thereby control the diversion of milk flow between the first and second channel. For example, rotating the removable protective cap 370 may cause the flow closure component 330 to rotate, causing the individual flaps or components of the flow closure component 330 to either dilate or fan out, or constrict or fold inward, depending on the directionality of the rotation. In other embodiments, other methods of transitioning the flow closure component 330 are contemplated, as will be readily understood by one of ordinary skill in the art.

The present disclosure is also directed to a method to operate an infant gavage feeding apparatus 100. In some embodiments, for example, the method can include attaching a gavage milk delivery component 115 to an infant feeding bottle 105 as illustrated in FIG. 1. The cord component 125 is positioned to releasably connect the gavage milk delivery component 115 to the infant feeding bottle 105 when the gavage milk delivery component 115 is not in use.

In some embodiments as illustrated in FIG. 4, the gavage milk delivery component 115 can include a frustoconical portion 155 and an elongate tube portion 150 connected to and extending outwardly and distally from the frustoconical portion 155. The elongate tube portion 150 can be positioned to connect with an enteral feeding tube 165 when positioned adjacent thereto in order to facilitate gavage feeding.

As illustrated in FIG. 2, the method to operate an infant gavage feeding apparatus 100 can also include removing a nipple 120 from a top portion 170 of the infant feeding bottle 105. The nipple 120 can be a standard baby nipple of any appropriate size, shape, or material as required for the needed purpose. As further illustrated in FIG. 2, the nipple 120 can be secured to the top portion 170 of the infant feeding bottle 105 via various attachment means such as snap fitting or screw fitting. In some embodiments, removing the nipple portion 120 can include, for example, rotating the nipple portion 120 on a threaded portion of the top portion 170 of the infant feeding bottle 105. In other embodiments, the nipple portion 120 can be removed from the infant feeding bottle 105 by any other acceptable means, such as by unsnapping or the like, as will be readily understood by one of ordinary skill in the art.

According to an embodiment of the present disclosure and illustrated in FIG. 2, the nipple 120 is removable from the top portion 170 of the infant feeding bottle 105 in order to allow attachment of a retaining ring 160 to the infant feeding bottle 105. In an embodiment, for example, the retaining ring 160 can be positioned to secure a base of the frustoconical portion 155 of the gavage milk delivery component 115 to the top portion 170 of the infant feeding bottle 105.

Figure 3:
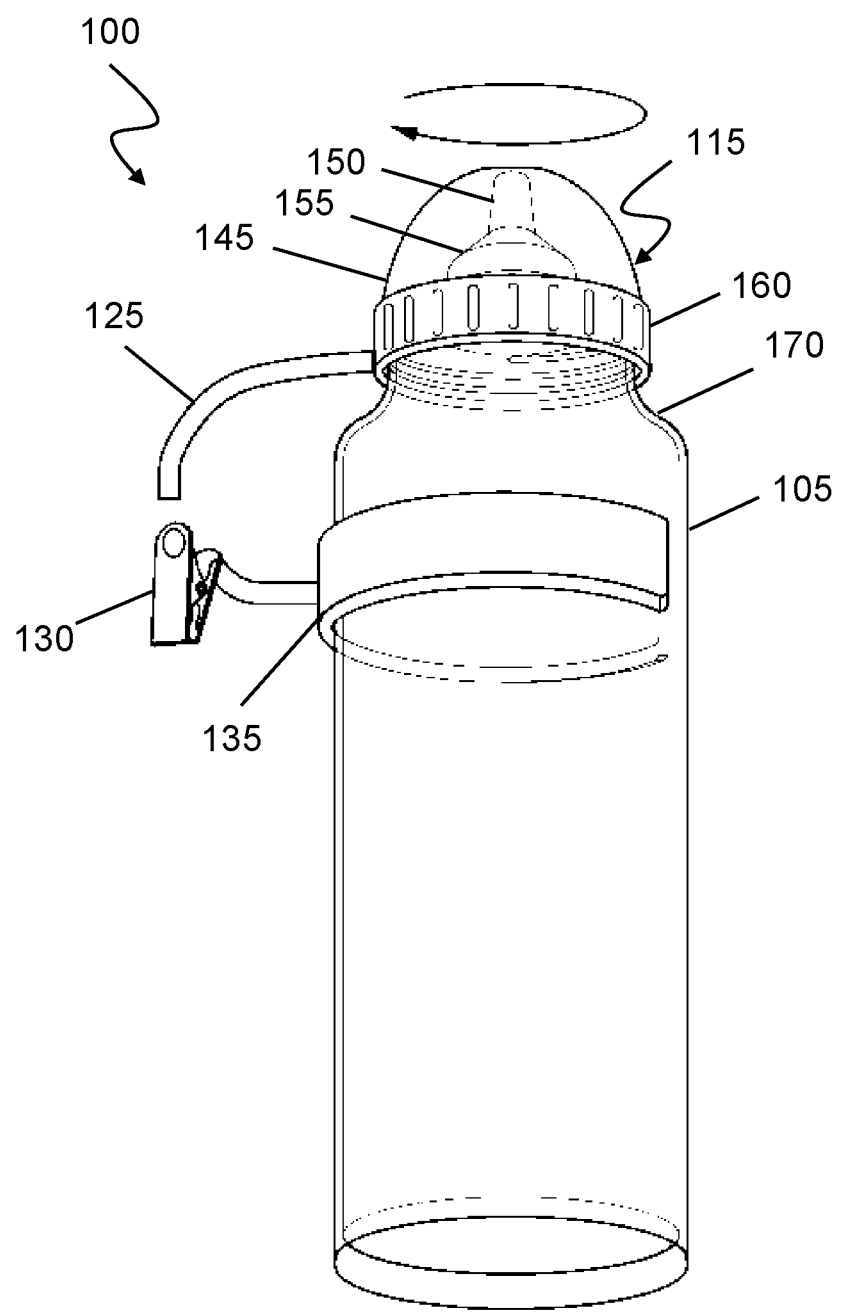
FIG. 3 is a perspective view of an infant gavage feeding apparatus having a gavage milk delivery component connected to an infant feeding bottle, according to an embodiment.

In some embodiments, for example, the method can further include replacing the removed nipple 120 with the gavage milk delivery component 115 as illustrated in FIG. 3. The gavage milk delivery component 115 can be secured to the top portion 170 of the infant feeding bottle 105 by a screw, snap, or other suitable connection, as will be readily understood by one of ordinary skill in the art.

As further illustrated in FIG. 3, the attachment of the retaining ring 160 to the infant feeding bottle 105 may be positioned such that tightening the retaining ring 160 to the top portion 170 of the infant feeding bottle 105 breaks the cord component 125 in order to disconnect the gavage milk delivery component 115 from the grip component 135. As the retaining ring 160 is rotated on the top portion 170 of the infant feeding bottle 105, the cord component 125 may be stretched and extended such that the weakest point of the cord component 125 is caused to break, thereby separating the gavage milk delivery component 115 from the infant feeding bottle 105.

As illustrated in FIG. 4, the method can also include fluidly connecting a distal end of the elongate tube portion 150 of the gavage milk delivery component 115 to a proximal end of the enteral feeding tube 165 and inverting the infant feeding bottle 105 to initiate a flow of milk from the infant feeding bottle 105 into the enteral feeding tube 165 via the gavage milk delivery component 115 in order to facilitate gavage feeding.

In some embodiments, for example, the method can further include attaching a retaining ring 160 to the infant feeding bottle 105, the retaining ring 160 securing a base of the frustoconical portion 155 of the gavage milk delivery component 115 to the top portion 170 of the infant feeding bottle 105. As illustrated in FIG. 2, prior to replacing the removed nipple 112 with the gavage milk delivery component 115, the method can further include removing a releasable seal 140 from a bottom of the retaining ring 160 to expose the base of the frustoconical portion 155 of the gavage milk delivery component 115 in order to allow the gavage milk delivery component 115 to be fluidly connected to the infant feeding bottle 105. The releasable seal 140 can be positioned at the bottom of the retaining ring 160 and a perimeter of the releasable seal 140 can be attached to a perimeter of the bottom of the retaining ring 160 thereby sealing the bottom of the retaining ring 160 in order to prevent contamination of an interior of the gavage milk delivery component 115.

In some embodiments as illustrated in FIG. 3, prior to replacing the removed nipple 112 with the gavage milk delivery component 115, the method can also include removing a removable protective cap 145 from the retaining ring 160 to expose the elongate tube portion 150 of the gavage milk delivery component 115 in order to allow coupling of the elongate tube portion 150 of the gavage milk delivery component 115 to the enteral feeding tube 165 when the removable protective cap 145 is removed. The removable protective cap 145 can be positioned to cover the gavage milk delivery component 115 when the removable protective cap 145 is affixed to the retaining ring 160 in order to prevent contamination of the elongate tube portion 150.

In some embodiments, for example, the method can also include attaching a grip component 135 to the infant feeding bottle 105. A proximal end of the cord component can secure the gavage milk delivery component 115 to the infant feeding bottle 105. The grip component 135 may be positioned at a distal end of the cord component 125, so as to connect the gavage milk delivery component 115 to the infant feeding bottle 105. The grip component 135 can include a stiff or flexible component that partially or wholly encircles the outer diameter of the infant feeding bottle 105. Additionally, the method can include attaching the retaining ring 160 to the infant feeding bottle 105, thereby breaking the cord component 125 when the retaining ring 160 is attached to the infant feeding bottle 105 in order to disconnect the gavage milk delivery component 115 from the grip component 135. The method can further include sliding the grip component 135 of the cord component 125 downwardly along a longitudinal axis of the infant feeding bottle 105 after the cord component 125 is detached from the gavage milk delivery component 115 in order to allow the infant gavage feeding apparatus 100 to be stably supported when the infant gavage feeding apparatus 100 is in an inverted position, as illustrated in FIG. 4.

As illustrated in FIG. 5, the method can further include attaching a clip 130 positioned on the cord component to a user 560 to secure the infant gavage feeding apparatus 100 in an inverted orientation in order to allow hands-free feeding. In other embodiments, the clip 130 can be used to attach the infant feeding bottle 105 to an IV pole, stand, or other furniture of device.

The present disclosure is also directed to a method to operate an alternate nipple feeding and gavage feeding apparatus in which a gavage milk delivery component and a nipple receiving component are arranged in a branched configuration.

In some embodiments, for example, the method can include removing a nipple 120 from a top portion 170 of the infant feeding bottle 105. The nipple 120 is removable from the top portion 170 of the infant feeding bottle 105 in order to allow attachment of an infant milk dual-delivery device 200 to the top portion 170 of the infant feeding bottle 105. The method can also include attaching the infant milk dual-delivery device 200 to the top portion 170 of the infant feeding bottle 105.

The infant milk dual-delivery device 200 can include a gavage milk delivery component 215. The gavage milk delivery component 215 can include a frustoconical portion 155 and an elongate tube portion 150 connected to and extending outwardly and distally from the frustoconical portion 155. The elongate tube portion 150, for example, can be positioned to connect with an enteral feeding tube 165 when positioned adjacent thereto in order to facilitate gavage feeding. The infant milk dual-delivery device 200 can also include a retaining ring 260 to secure a base of the gavage milk delivery component 215 to the top portion 170 of the infant feeding bottle 105. The infant milk dual-delivery device 200 can further include a nipple receiving component positioned to allow the nipple 110 to be removably connected to the infant milk dual-delivery device 200 in order to facilitate nipple feeding. In some embodiments, the gavage milk delivery component 215 and the nipple receiving component 220 can be positioned in a branched configuration in order to alternately facilitate nipple feeding and gavage feeding.

The method can also include connecting the nipple 112 to the nipple receiving component 220 in order to facilitate nipple feeding and inverting the infant feeding bottle 105 to initiate a flow of milk from the infant feeding bottle 105 alternately into the nipple 112 in order to facilitate nipple feeding and into the gavage milk delivery component 215 in order to facilitate gavage feeding. For example, the infant feeding bottle 105 may be inverted and positioned such that the nipple 112 is positioned downward, while the gavage milk delivery component 215 is positioned upward, such that milk is allowed to flow by gravity from the infant feeding bottle 105 into the nipple 112, without escaping through the gavage milk delivery component 215. Alternately, the infant feeding bottle 105 may be inverted and positioned such that the gavage milk delivery component 215 is positioned downward, while the nipple 112 is positioned upward, such that milk is allowed to flow by gravity form the infant feeding bottle 105 into the gavage milk delivery component 215, without escaping through the nipple 112.

In some embodiments, for example, the method can further include positioning a flow closure component 225 in a first position in order to facilitate nipple feeding. The flow closure component 225 can be positioned in order to divide a milk flow path from the infant feeding bottle 105 into a first channel and a second channel. According to an embodiment of the present disclosure, the first channel may form the milk flow path from the infant feeding bottle 105 to the nipple 110. The method can further include positioning a flow closure component 225 in a second position in order to facilitate gavage feeding. The second position may open the second channel forming the milk flow path from the infant feeding bottle 105 to the gavage milk delivery component 215. A controller 230 may be positioned to transition the flow closure component 225 between the first position and the second position. Such transition can include any of rotation, sliding, switching, or the like, as will be readily understood by one of ordinary skill in the art.

The present disclosure is also directed to a method to operate an alternate nipple feeding and gavage feeding apparatus whereby a gavage milk delivery component and a nipple receiving component are arranged in series, in a stacked configuration.

In one or more embodiments, the method an include removing a nipple 112 from a top portion 170 of the infant feeding bottle 105. The nipple 120 is removable from the top portion 170 of the infant feeding bottle 105 in order to allow attachment of an infant milk dual-delivery device 300 to the infant feeding bottle 105. The method can further include attaching the infant milk dual-delivery device 300 to the top portion 170 of the infant feeding bottle 105.

According to an embodiment of the present disclosure, the infant milk dual-delivery device 300 can include a gavage milk delivery component 315. The gavage milk delivery component 315 can include a frustoconical portion 155 and an elongate tube portion 150 connected to and extending outwardly and distally from the frustoconical portion 155. The elongate tube portion 150 can be positioned to connect with an enteral feeding tube 165 when positioned adjacent thereto in order to facilitate gavage feeding. In some embodiments, for example, the infant milk dual-delivery device 300 can include a retaining ring 360 to secure a base 325 of the gavage milk delivery component 315 to the top portion 170 of the infant feeding bottle. The infant milk dual-delivery device 300 can further include a nipple receiving component 320 positioned to allow the nipple 110 to be removably connected to the infant milk dual-delivery device 300 in order to facilitate nipple feeding. In an embodiment, the gavage milk delivery component 315 and the nipple receiving component 320 can be positioned in a stacked configuration in order to alternately facilitate nipple feeding and gavage feeding.

Figure 10:
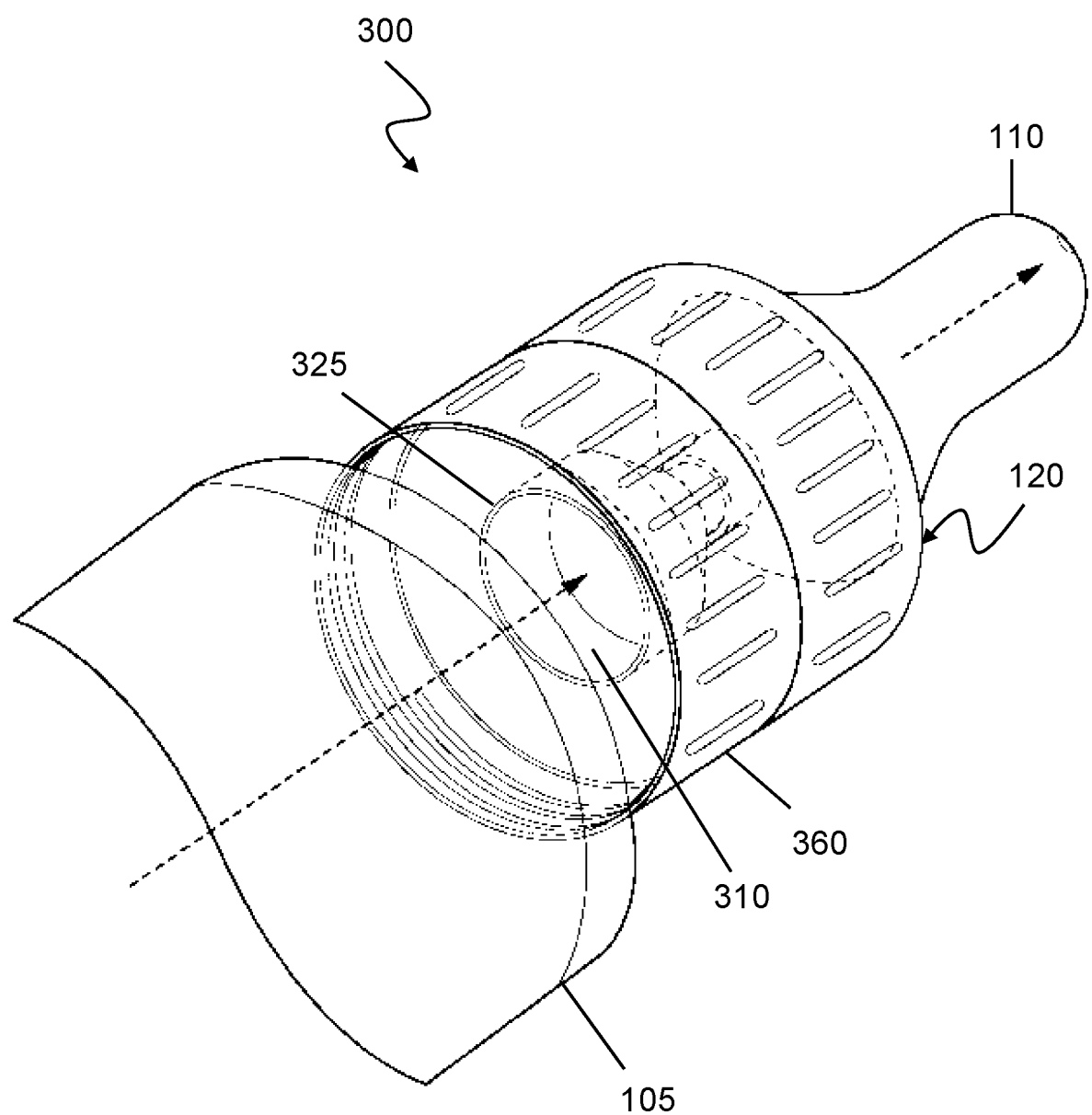
FIG. 10 is a partial rear perspective view of an infant milk dual-delivery device in a stacked configuration showing a nipple connected to a nipple receiving component and a funnel connected to the gavage milk delivery component to facilitate nipple feeding, according to an embodiment.
Figure 11:
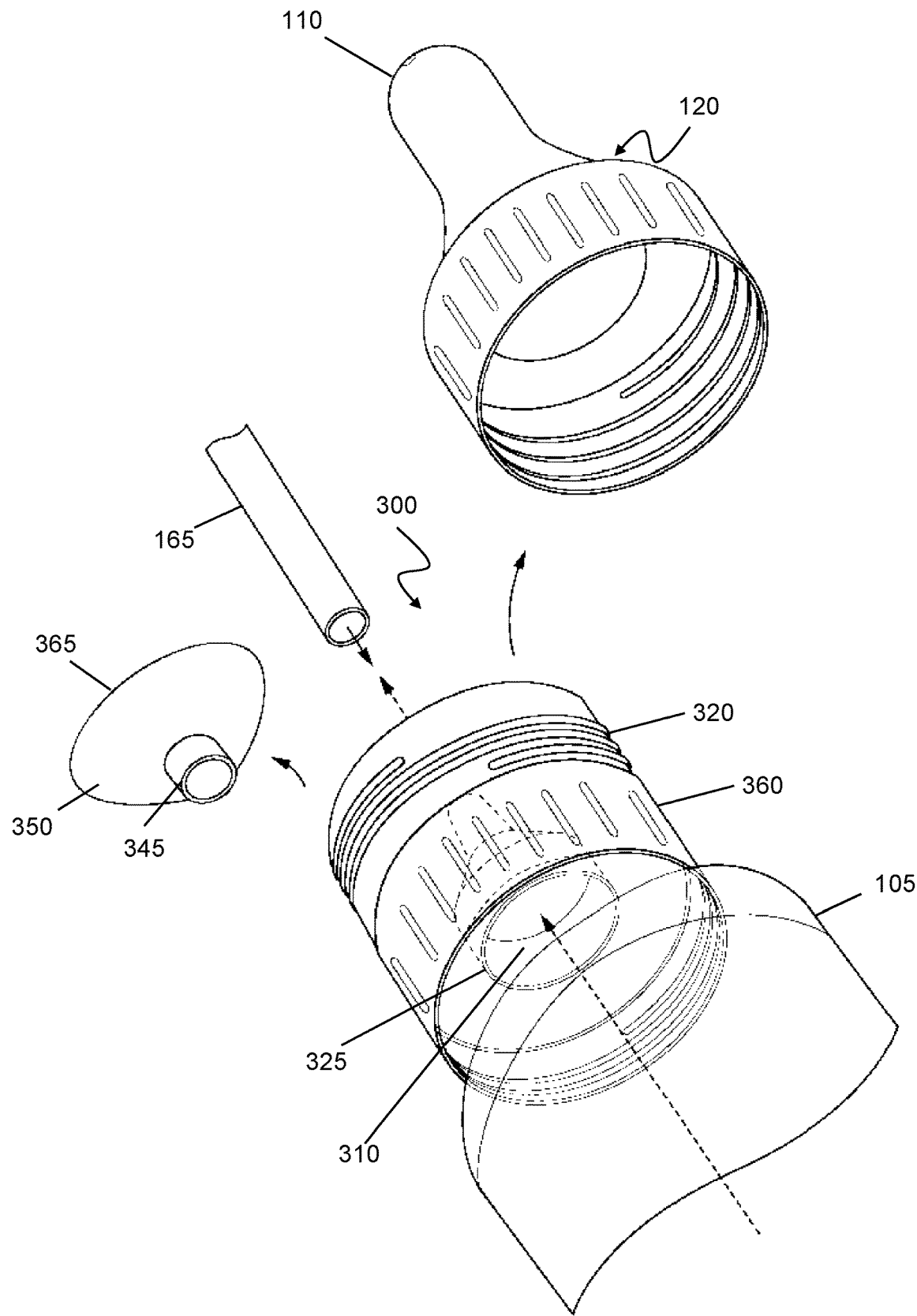
FIG. 11 is a partial rear perspective view of an infant milk dual-delivery device in a stacked configuration, a nipple, an enteral feeding tube, and a funnel, according to an embodiment.

In some embodiments, for example, the method can further include inserting the apex of a funnel 345 into a distal end of the elongate tube portion 150 of the gavage milk delivery component 315. As illustrated in FIG. 8, for example, the base 350 of the funnel 365 can be positioned to circumvent a base of the nipple 110 when positioned thereon in order to allow milk in the nipple 110 to flow back into the infant feeding bottle 105 through the elongate tube portion 150 of the gavage milk delivery component 315 when the infant feeding bottle 105 is positioned in an upright position in order to avoid loss of milk. As illustrated in FIG. 10, the method can also include connecting the nipple 110 to the nipple receiving component 320 in order to facilitate nipple feeding. The method can further include inverting the infant feeding bottle 105 to initiate a flow of milk from the infant feeding bottle 105 into the nipple 110 in order to facilitate nipple feeding.

In the embodiment illustrated in FIG. 9, for example, the method can further include disconnecting the nipple 110 from the nipple receiving component 320. As further illustrated in FIG. 9, the method an also include removing the funnel 365 from the gavage milk delivery component 315 and fluidly connecting the distal end of the elongate tube portion 150 of the gavage milk delivery component 315 to a proximal end of the enteral feeding tube 165. The method can additionally include inverting the infant feeding bottle 105 to initiate a flow of milk from the infant feeding bottle 105 into the enteral feeding tube 165 in order to facilitate gavage feeding, for example as illustrated in FIG. 5.

Figure 14:
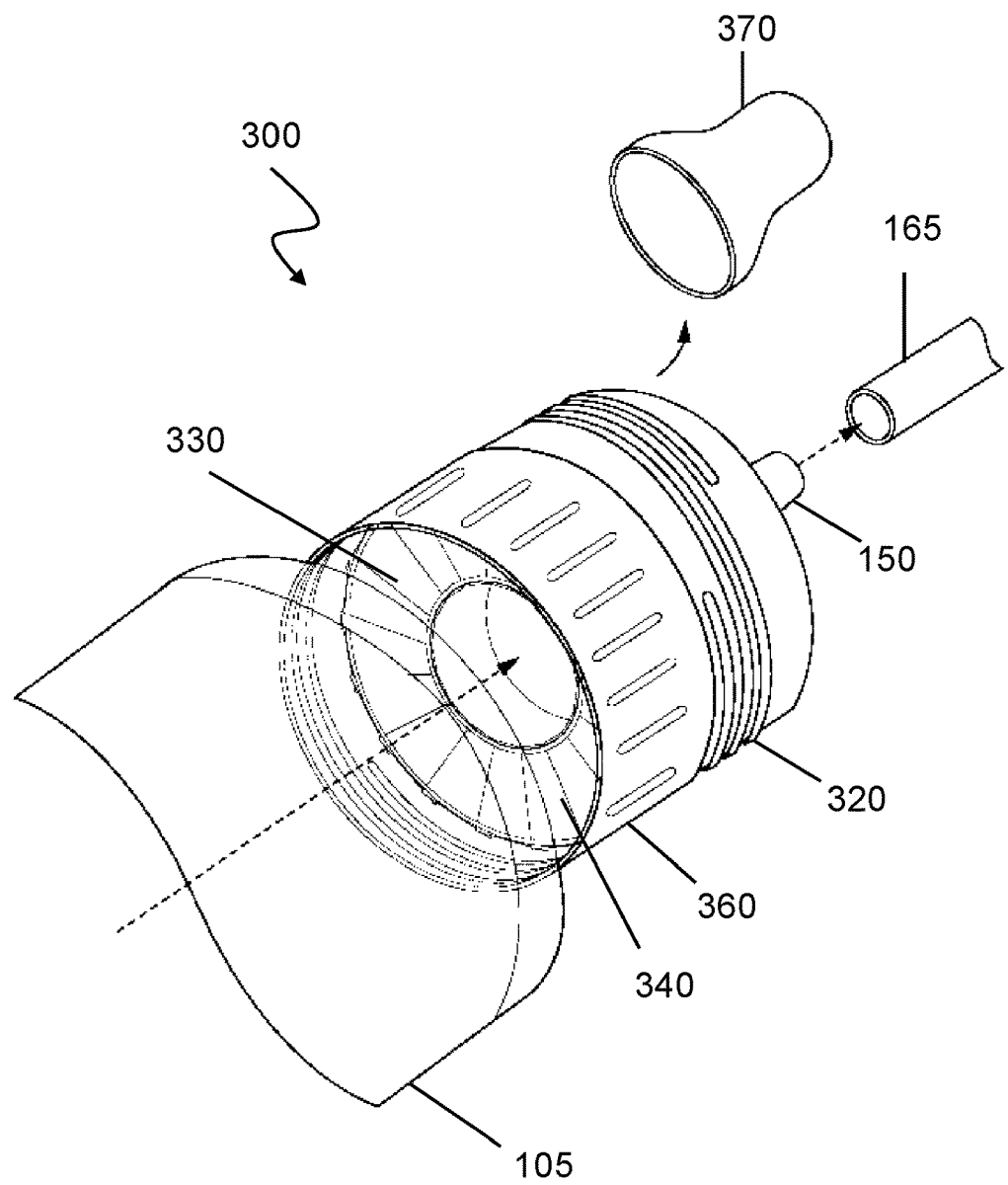
FIG. 14 is a partial rear perspective view of an infant milk dual-delivery device in a stacked configuration, an enteral feeding tube, and a removable protective cap, according to an embodiment.

In some embodiments, the method can further include connecting the nipple 110 to the nipple receiving component 320 in order to facilitate nipple feeding, as illustrated in FIG. 12. The method can also include positioning a flow closure component 330 in a first position to open a first channel in order to allow the milk to flow from the infant feeding bottle 105 through an area circumventing an opening 340 in the base 325 of the gavage milk delivery component 315 and into the nipple 110. In addition, the method can include inverting the infant feeding bottle 105 to initiate the flow of milk from the infant feeding bottle 105 into the nipple 110 in order to facilitate nipple feeding. As illustrated in FIG. 14, for example, the method can additionally include disconnecting the nipple 110 from the nipple receiving component 320 and fluidly connecting a distal end of the elongate tube portion 150 of the gavage milk delivery component 315 to a proximal end of the enteral feeding tube 165. In some embodiments, the method can also include positioning the flow closure component 330 in the second position to open the second channel in order to allow milk to flow from the infant feeding bottle 105 through the opening 310 in the base 325 of the gavage milk delivery component 315, as illustrated in FIG. 13. The method can further include inverting the infant feeding bottle 105 to initiate the flow of milk from the infant feeding bottle 105 into the enteral feeding tube 165 in order to facilitate gavage feeding.

This application is a continuation-in-part of PCT Application No. PCT/US19/21334, filed Mar. 8, 2019, titled "APPARATUS, DEVICE, METHOD, AND KIT FOR INFANT GAVAGE FEEDING," which claims priority to, and the benefit of, U.S. Provisional Application No. 62/640,346, filed Mar. 8, 2018, titled "APPARATUS, DEVICE, METHOD, AND KIT FOR INFANT GAVAGE FEEDING," each of which is incorporated herein by reference in its entirety.

What is claimed is:

1. An infant milk dual-delivery device attachable to an infant feeding bottle, the device comprising:
   a nipple receiving component which allows for the removable attachment of a nipple;
   a gavage milk delivery component with a frustoconical portion; and an elongate tube portion connectable to an enteral feeding tube; wherein the nipple receiving component and the gavage milk delivery component are in a branched configuration separated by an angle less than or equal to ninety degrees; and
   a retaining ring of fluid connection with the gavage milk delivery component and the nipple receiving component in a and removably connected to a top portion of the infant feeding bottle, wherein the positioning of the infant milk dual-delivery device allows for seamless transition between only nipple feeding or only gavage feeding.

2. The device of claim 1, the device further comprising:
   a flow closure component, the flow closure component positioned so as to divide a milk flow path from the infant feeding bottle into a first channel and a second channel, the first channel comprising the milk flow path from the infant feeding bottle to the nipple, and the second channel comprising the milk flow path from the infant feeding bottle to the gavage milk delivery component, wherein the first channel facilitates nipple feeding and the second channel facilitates gavage feeding; and a controller positioned to transition the flow closure component between a first position to facilitate nipple feeding via the first channel and a second position to facilitate gavage feeding via the second channel.

3. A method to operate the infant milk dual-delivery device of claim 1, the method comprising:

attaching a nipple to a nipple receiving component of the infant milk dual-delivery device, the infant milk dual-delivery device containing (1) the nipple receiving component, (ii) a gavage milk delivery component with a frustoconical portion and an elongate tube portion connectable to an enteral feeding tube, and (ii1) a retaining ring in fluid connection with the gavage milk delivery component and the nipple receiving component and removably connected to an infant feeding bottle;

attaching the enteral feeding tube to the gavage milk delivery component;

attaching the infant milk dual-delivery device to the infant feeding bottle via the retaining ring; and inverting the infant feeding bottle and adjusting the position of the infant milk dual-delivery device to initiate a flow of milk from the infant feeding bottle into the nipple to facilitate nipple feeding only or alternately into the gavage milk delivery component to facilitate gavage feeding only, wherein, no fluid flows into the nipple receiving component during gavage feeding and no fluid flows into the gavage milk delivery component during nipple feeding.

4. The method of claim 3, the method further comprising:

positioning a flow closure component in a first position so as to facilitate nipple feeding, the flow closure component positioned so as to divide a milk flow path from the infant feeding bottle into a first channel and a second channel, the first channel forming the milk flow path from the infant feeding bottle to the nipple; and positioning the flow closure component in a second position so as to facilitate gavage feeding, the second position opening the second channel forming the milk flow path from the infant feeding bottle to the gavage milk delivery component, wherein a controller is positioned to transition the flow closure component between the first position and the second position.

5. The method of claim 4, the method further comprising:

positioning a flow closure component in a first position to open a first channel so as to allow the milk to flow from the infant feeding bottle through an area circumventing an opening in the second base of the gavage milk delivery component and into the nipple;

inverting the infant feeding bottle to initiate the flow of milk from the infant feeding bottle into the nipple so as to facilitate nipple feeding;

disconnecting the nipple from the nipple receiving component;

fluidly connecting a distal end of the elongate tube portion of the gavage milk delivery component to a proximal end of the enteral feeding tube;

positioning the flow closure in the second position to open a second channel so as to allow milk to flow from the infant feeding bottle through the opening in the second base of the gavage milk delivery component; and inverting the infant feeding bottle to initiate the flow of milk from the infant feeding bottle into the enteral feeding tube so as to facilitate gavage feeding.

* * * * *